United States Patent
Bettenhausen et al.

(10) Patent No.: US 7,717,264 B2
(45) Date of Patent: May 18, 2010

(54) MODULAR CONTAINER FOR MEDICAL INSTRUMENTS AND IMPLANTS WITH EXTRUDED FLEXIBLE BRACKET AND RIGID HOLDERS

(75) Inventors: Todd E. Bettenhausen, Indianapolis, IN (US); Cary A. Bettenhausen, Indianapolis, IN (US)

(73) Assignee: ContainMed, Inc., Speedway, IN (US)

( * ) Notice: Subject to any disclaimer, the term of this patent is extended or adjusted under 35 U.S.C. 154(b) by 411 days.

(21) Appl. No.: 11/747,569

(22) Filed: May 11, 2007

(65) Prior Publication Data

US 2007/0205123 A1    Sep. 6, 2007

(51) Int. Cl.
 B65D 83/10  (2006.01)
 A61L 2/00   (2006.01)
(52) U.S. Cl. .................................. 206/370; 422/300
(58) Field of Classification Search ............... 206/370, 206/439, 363; 422/300, 297; 211/85.13; 248/220.41, 213.2, 220.31
See application file for complete search history.

(56) References Cited

U.S. PATENT DOCUMENTS

| | | | |
|---|---|---|---|
| 4,304,382 A * | 12/1981 | Jelen | 248/220.42 |
| 4,798,292 A | 1/1989 | Hauze | |
| 4,915,913 A | 4/1990 | Williams et al. | |
| 5,384,103 A * | 1/1995 | Miller | 422/310 |
| 5,540,901 A | 7/1996 | Riley | |
| 5,681,539 A | 10/1997 | Riley | |
| 5,725,097 A | 3/1998 | Bettenhausen et al. | |
| 5,759,502 A * | 6/1998 | Spencer et al. | 422/300 |
| 5,896,987 A | 4/1999 | Bettenhausen | |
| 6,048,503 A | 4/2000 | Riley et al. | |
| 6,099,812 A * | 8/2000 | Allen et al. | 422/300 |
| 6,116,452 A | 9/2000 | Hamel et al. | |
| 6,164,738 A | 12/2000 | Dane et al. | |
| 6,439,625 B1 | 8/2002 | Schainholz et al. | |

* cited by examiner

Primary Examiner—J. Gregory Pickett
(74) Attorney, Agent, or Firm—Woodard, Emhardt, Moriarty, McNett & Henry LLP

(57) ABSTRACT

A system for organizing, protecting, sterilizing, storing and delivery of surgical instruments, implants and related devices. Post and button fasteners are removably mounted to a tray and hold rigid and flexible bracketry for securing devices within the assembly. A flexible bar for holding items is mounted by a pair of rigid brackets in turn mounted either directly to the tray floor or to a base wall positioned atop the tray floor.

18 Claims, 28 Drawing Sheets

MODULAR CONTAINER FOR MEDICAL INSTRUMENTS AND IMPLANTS WITH EXTRUDED FLEXIBLE BRACKET AND RIGID HOLDERS

BACKGROUND OF THE INVENTION

The present invention relates generally to the field of containers and cases for holding surgical instruments, implants and devices and to the brackets for holding the instruments, implants and devices.

DESCRIPTION OF THE PRIOR ART

Various types of containers and cases have been provided to organize surgical instruments, implants and other medical devices. These items must not only be organized but protected from damage. Likewise, the items must be sterilized, stored and then delivered for ready use. In our U.S. Pat. No. 5,725, 097, we have disclosed an instrument cassette and sterile wrap assembly composed of a tray and a lid mounted thereto. In our U.S. Pat. No. 5,759,502 we have disclosed an instrument cassette having a mechanism to prevent lateral movement of the medical instrument when positioned within the cassette. In the U.S. Pat. No. 5,896,987 the tray is provided with downwardly extending feet that are nestable within recesses provided in the tray cover located there beneath. In our U.S. Pat. No. 6,164,738 the storage and sterilization tray assembly is designed to be slidably mounted on a horizontally extending rack.

The sterilization and storage tray assemblies must be modified or tailored to the particular size and configuration of the instruments, implants and devices to be held within the tray. Various types of bracketry and holders are typically mounted within the tray assembly with the configuration of the brackets depending upon the devices to be held within the assembly. In order to utilize the tray assembly in a variety of different applications, it is desirable to provide a tray assembly having internal brackets that may be easily moved or changed depending upon the devices to be held by the brackets. Disclosed herein is such a tray assembly.

One such bracket we have devised is shown in FIGS. 29-34. The bracket shown is particularly useful in partitioning the container into multiple compartments through the use of a bar mounted to a plurality of rigid brackets holding the bar to a base plate or the floor of a container. The bar is produced from a flexible material, such as, silicone rubber thereby allowing the bar to be cut and shaped to hold a variety of differently configured medical items. The length of a bracket produced from a flexible material is limited when vertical posts are used to mount the bracket since the material will flex an undesirable amount. The flexible bar shown in FIG. 29 on the other hand is secured along its length thereby limiting the amount of flexibility.

SUMMARY OF THE INVENTION

One embodiment of the present invention is a bracket arrangement to hold medical items on a base wall including elongated first and second brackets. The first bracket has a first main body with a plurality of first feet extending there beneath. The first main body has a first plate extending the length thereof and arranged relative to the first feet at a first angle so that when the first feet are mounted to a base wall, the first plate is arranged relative to the base wall at the first angle. Likewise, the second bracket has a second main body with a plurality of second feet extending there beneath. The second main body has a second plate extending parallel to the first plate. The second plate is arranged relative to the second feet at a second angle so that when the second feet are mounted to the base wall, the second plate is arranged relative to the base wall at the second angle. An elongated bar of flexible material extends along the length of the first and second brackets and has a lower edge portion releasably holdable between the brackets by the first and second plates.

DESCRIPTION OF THE PREFERRED EMBODIMENTS

Figure 1:
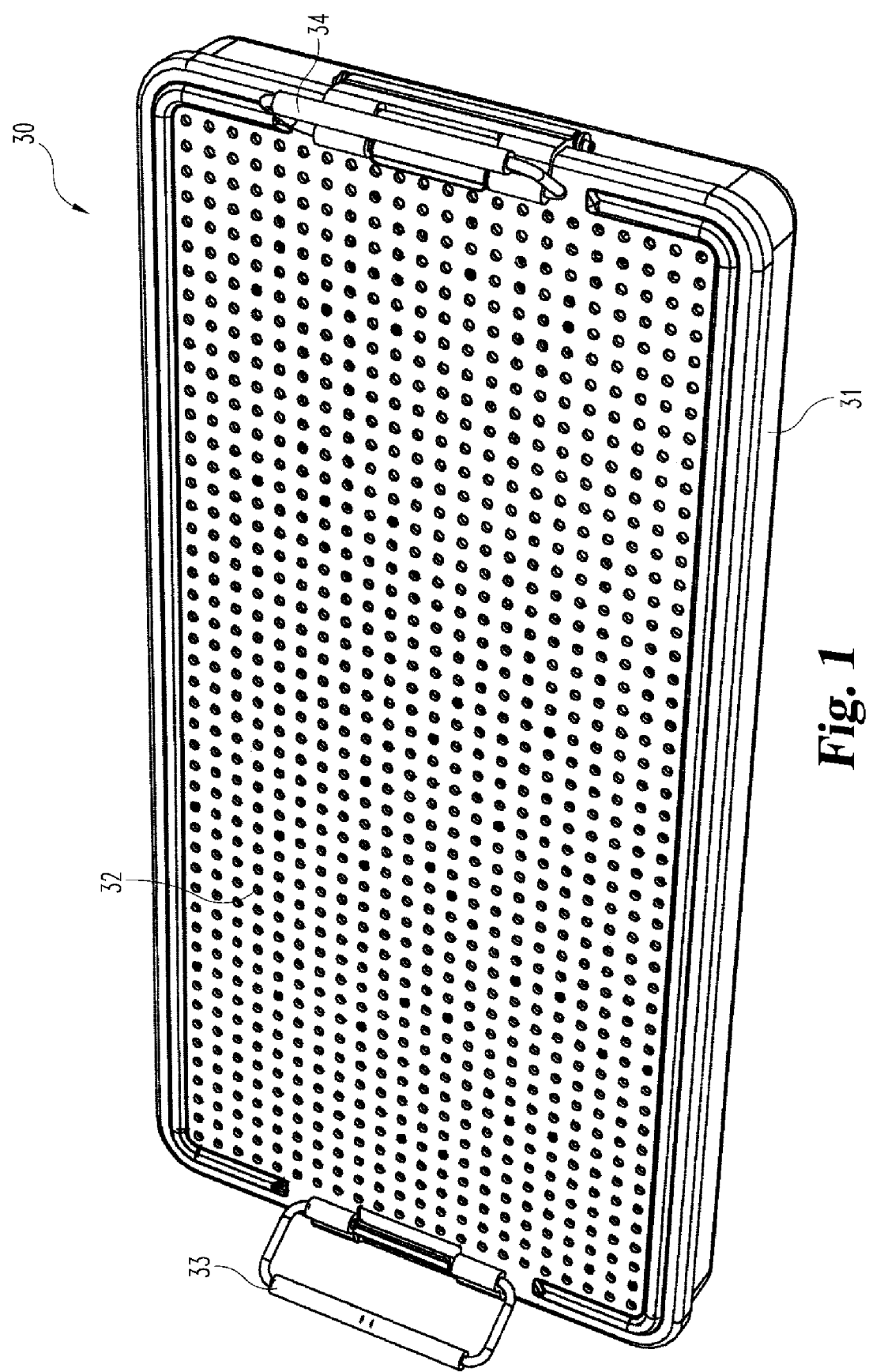
FIG. 1 is a perspective view of a tray assembly incorporating the present invention.
Figure 2:
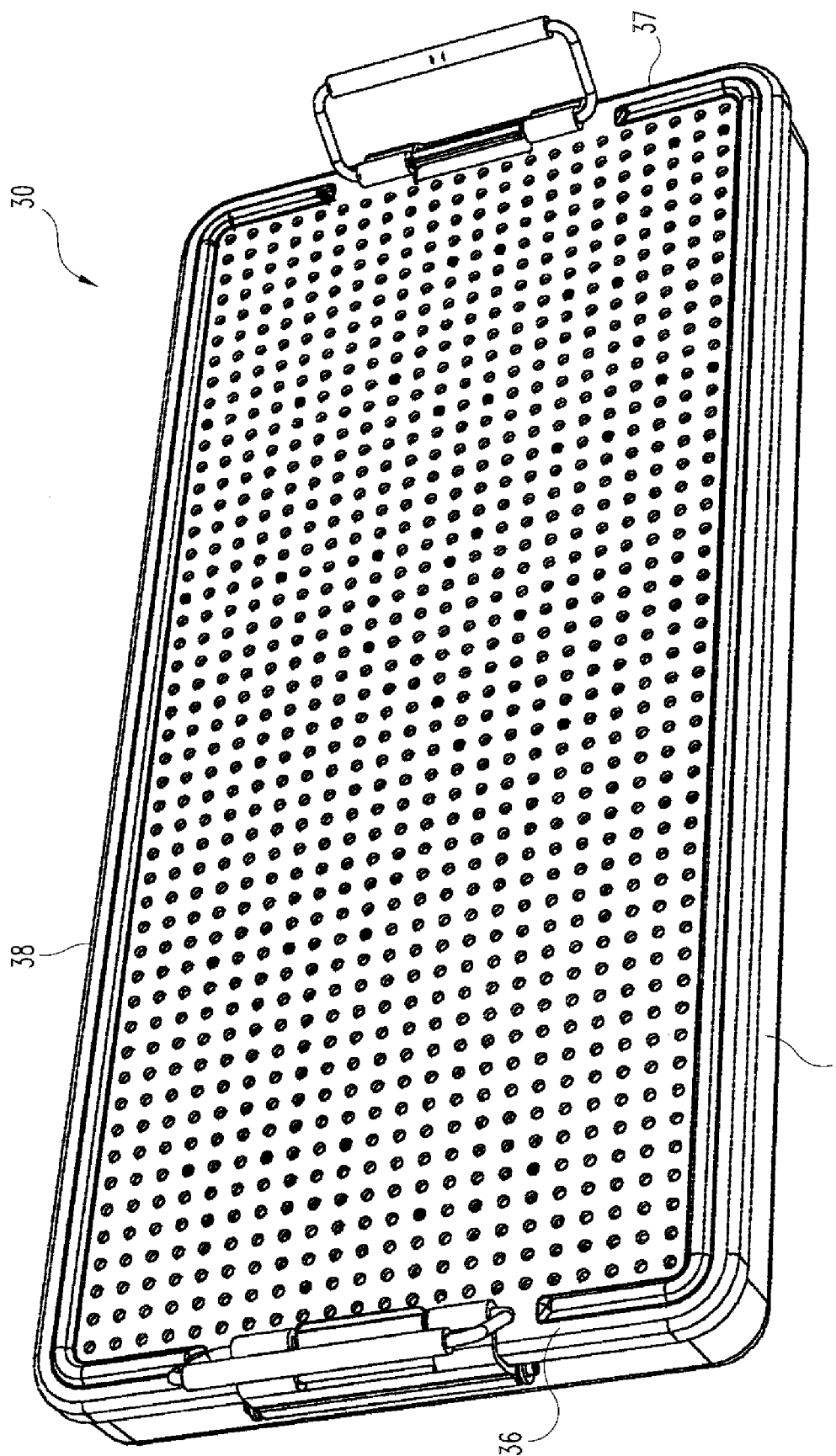
FIG. 2 is the same view as FIG. 1 illustrating the tray assembly from a different perspective.

For the purposes of promoting an understanding of the principles of the invention, reference will now be made to the embodiments illustrated in the drawings and specific language will be used to describe the same. It will nevertheless be understood that no limitation of the scope of the invention is thereby intended; such alterations and further modifications in the illustrated device, and such further applications of the principles of the invention as illustrated therein being contemplated as would normally occur to one skilled in the art to which the invention relates.

Referring to FIG. 1, there is shown a versatile storage and delivery system incorporating the present invention. The system includes a container 30 for the organization, protection, sterilization, storage, and delivery of surgical instruments, implants, and related devices.

Container 30 includes a perforated tray 31 and an optional, identically perforated cover 32 removably secured thereto by a pair of handle assemblies 33 and 34. The tray 31 (FIG. 5) has a perforated floor 35 joined to a pair of end walls 36 and 37 and a pair of side walls 38 and 39 with the end walls and side walls extending outwardly from the floor forming a cavity 40 into which may be located surgical instruments, implants and related devices.

Movable internal posts and buttons are located within the tray and retain rigid and flexible brackets and supports for holding the surgical instruments, implants and related devices within the tray. A fixture is first used to hold the posts in position for subsequent installation within the tray.

Figure 3:
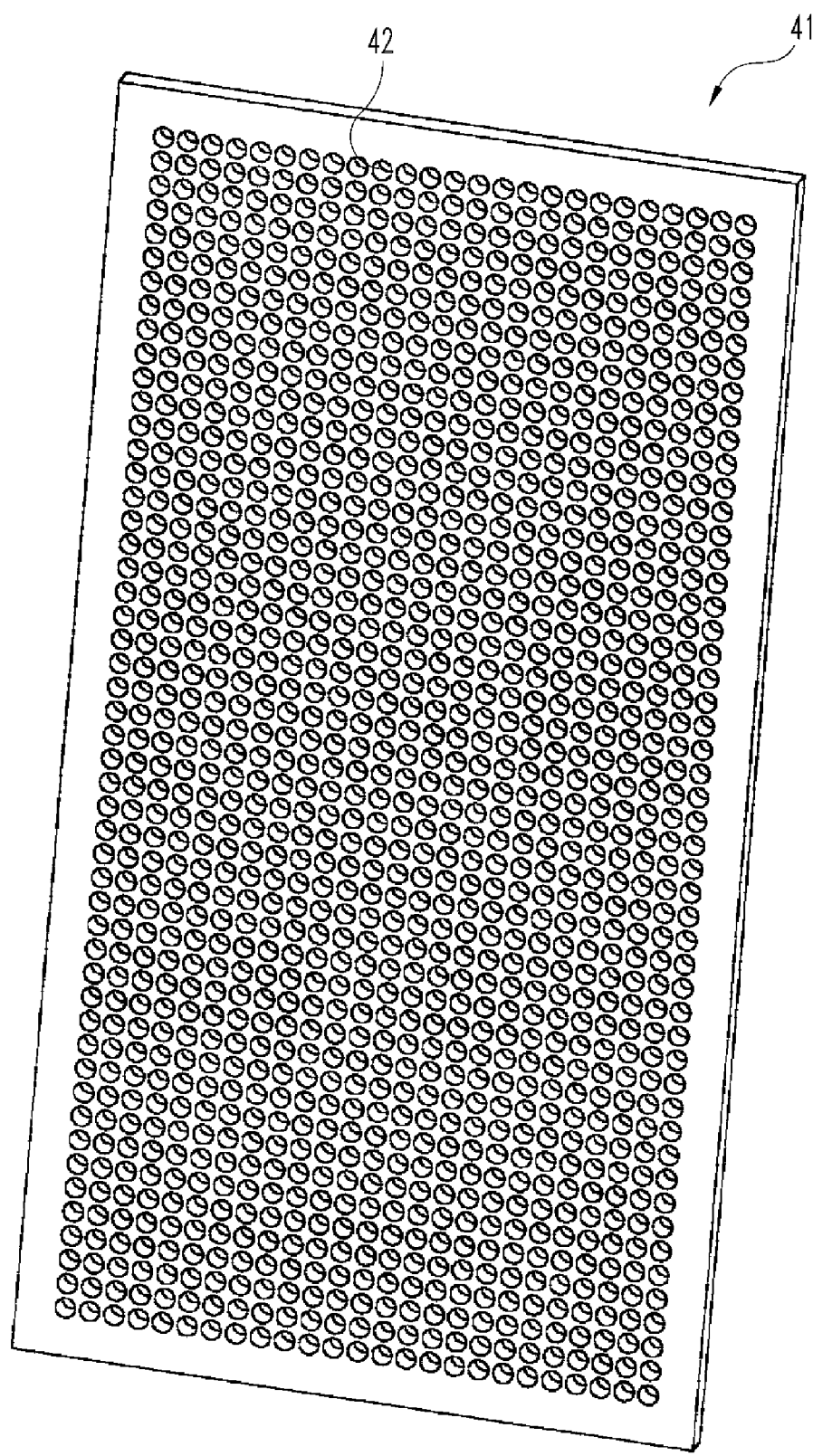
FIG. 3 is a front perspective view of a fixture utilized in installing internal components within the assembly of FIG. 1.

Fixture 41 (FIG. 3) is a flat plate having a plurality of holes 42 matching and alignable with the plurality of holes 52 provided in floor 35 (FIG. 5) of the tray. The tray and components may be assembled prior to shipment and use. Fixture 41 is utilized to configure or reconfigure the tray to the particular use.

Figure 8:
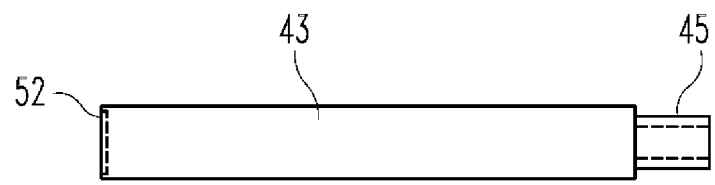
FIG. 8 is an enlarged view of one embodiment of a fixture post.
Figure 15:
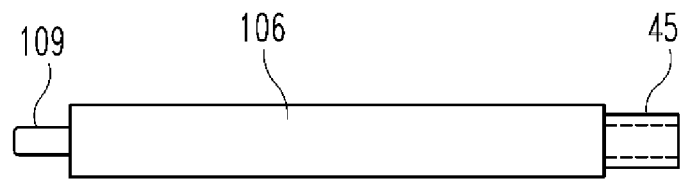
FIG. 15 is an enlarged view of another embodiment of a fixture post.
Figure 16:
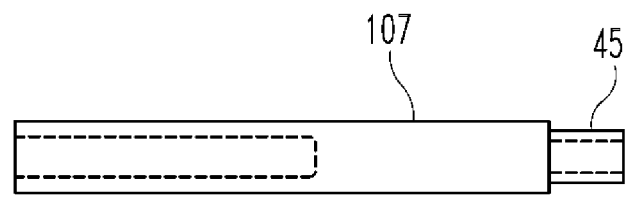
FIG. 16 is an enlarged view of yet another embodiment of a fixture post.

A plurality of cylindrical fixture posts 43, 106 & 107 (FIGS. 8, 15 & 16) are mounted to fixture 41. Each post 43, 106 & 107 includes a reduced diameter first end 45 sized to closely fit through holes 42 of fixture 41. Ends 45 are removably mounted to fixture 41 by conventional means. For example, each end 45 may have an internally threaded hole to receive a threaded bolt, the head of the bolt preventing disengagement of the post from the fixture. Likewise, a variety of snap rings and other devices may be used. As an alternative, external threads may be provided on ends 45 that extend through the fixture being threadedly received by internally threaded nuts provided on the opposite side of the fixture.

Figure 4:
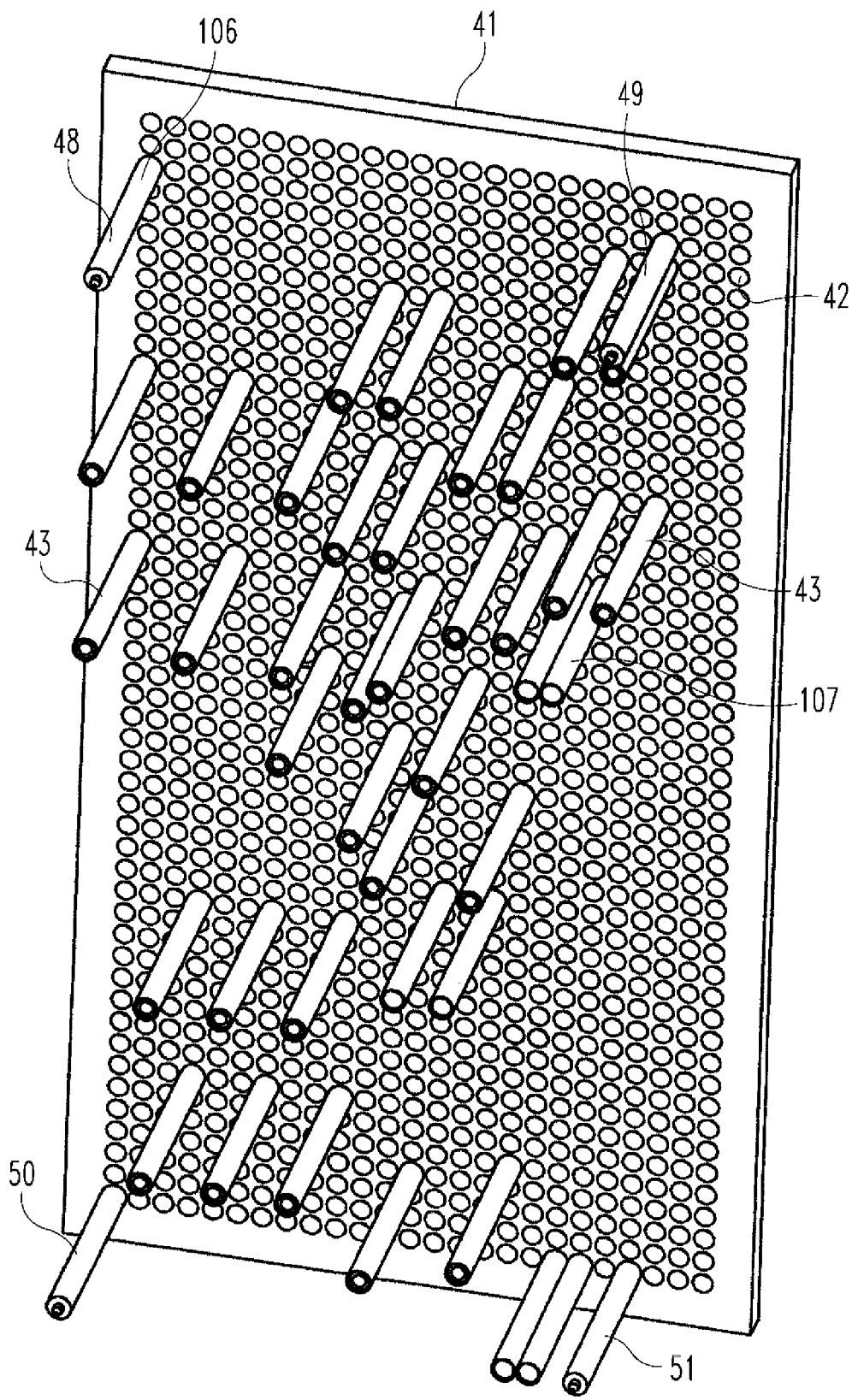
FIG. 4 is the same view as FIG. 3 only showing vertical posts mounted to the fixture and used to locate and assemble internal components within the tray assembly.

Fixture 41 is placed on a supporting work surface, such as a bench, etc., with the posts 43, 106 & 107 facing outward in the same direction as depicted in FIG. 4. Posts 106 serve as alignment posts with respect to the fixture and tray 31. In the embodiment depicted in FIG. 4, four such posts 106 are utilized and are shown as posts 48, 49, 50 and 51. These four posts are spaced apart to be positioned in the four corners of tray 31. The outer distal end 109 (FIG. 15) of each post 106 has a reduced diameter to extend through the holes 52 of the tray floor 35 once the tray is inverted and temporarily mounted to the outwardly extending posts of fixture 41.

Figure 9:
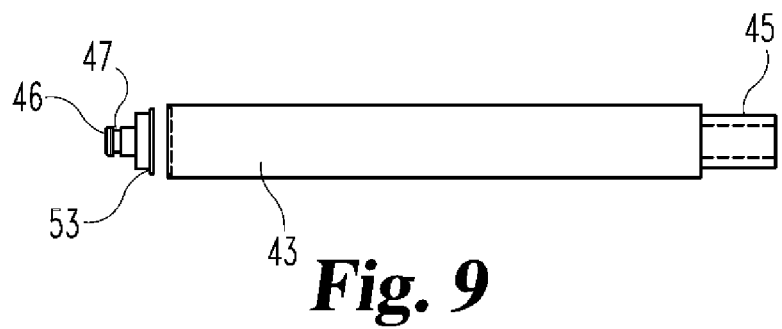
FIG. 9 is the same view as FIG. 8 only with a fastening button shown positioned to be inserted on the post for installation on the tray.

Fixture posts 43 have ends 52 that are counter bored to receive the heads of button fasteners 53 (FIG. 9) with the shanks 46 extendable through the tray floor 35. Shanks 46 have grooves to receive snap rings or may be externally threaded to receive an internally threaded fastener. Fixture posts 43 are used to install the button fasteners 53 on the tray as will be described latter in this specification.

Fixture posts 107 (FIG. 16) are hollow and internally sized to slidably receive bracket mounting posts 108 (FIG. 17) Once posts 43, 106 and 107 are mounted to the fixture, the bracket mounting posts 108 are positioned in the hollow fixture posts 107 and button fasteners 53 are positioned in the ends 52 of fixture posts 43.

Bracket mounting posts 108 are solid and include a cylindrical body with opposite ends 111 and 112. End 111 has a reduced diameter and is sized to fit through the optional cover 32 when mounted to tray 31. Post 108 has enlarged portions 113 and 114, that are ring-shaped in the preferred embodiment, adjacent ends 111 and 112 that act to restrain a flexible bracket mounted thereon and to be described later in this specification. End 112 has a reduced diameter portion 118 extendable through the floor of the tray with a groove 115 provided thereon to receive a retaining ring mounting the post to the tray floor. Other techniques may be utilized to secure post 108 to the tray floor. A variety of retaining rings are available. For example, one such ring is available from Truarc Company, LLC, 70 East Willow Street, Millburn, N.J., under Truarc Part No. 5304-15. Other means may be utilized to secure ends 112 and 46 to floor 35, such as described for the attachment of end 45 to fixture 41.

Post portion 116 (FIGS. 17 and 18) has a diameter greater than end 112 forming shoulder 110 but less than the main body of the post forming shoulder 117. Shoulder 117 abuts against the upwardly facing surface of wall 120 of bracket 70 whereas shoulder 110 abuts against the upwardly facing surface of floor 35 thereby cooperatively with the retaining ring on the opposite side of the tray floor holding the post in an upright and fixed position.

Posts 108 and button fasteners 53 (FIG. 5) are used to removably mount a plurality of flexible brackets 56 and rigid brackets 55 and 70 to the floor 35 of the tray. Button fastener 53 is designed to hold planer surfaces in mated contact including but not limited to rigid brackets and overlapping joints, such as those present at the corners of enclosures fabricated from folded sheet. Post 108 provides a cylindrical projection that occupies most of the vertical distance between floor 35 and the optional cover and locates the flexible brackets using the passages present at the ends of the brackets. Alternatively, posts 108 extend through the mid or other points of the brackets. The flexible and rigid brackets removably hold the various surgical instruments, implants and other devices in the tray.

Figure 19:
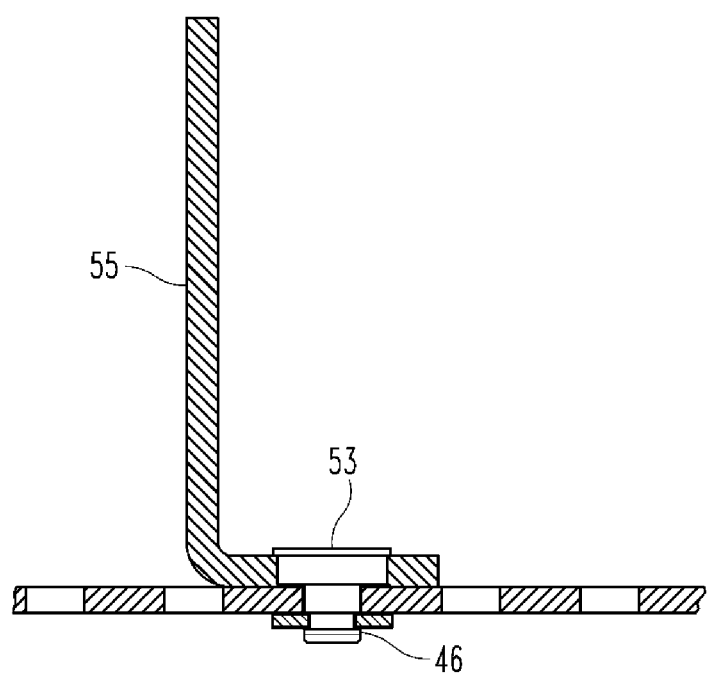
FIG. 19 is a cross sectional view taken along the line 19-19 of FIG. 6 and viewed in the direction of the arrows.

As an example, right angle rigid bracket 55 (FIG. 5) has a first wall 58 parallel to and removably mounted atop floor 35 by a pair of button fasteners 53 having an enlarged head positioned adjacent wall 58 with the end 46 (FIG. 19) of each button fastener extending through wall 58 and holes 52 of floor 35. A variety of techniques may be used to removably secure the shank of the button fastener to floor 35. For example, the shanks may be externally threaded and receive internally threaded nuts positioned on the opposite side of floor 35. The vertically extending bracket wall 60 includes a top end 61 with openings 62 formed therein to releasably receive and hold the ends 63 of items 64 and 65. The shape and configuration of openings 62 may be varied depending upon the size and configuration of the instrument, implant or other device to be held by the bracket.

Figure 17:
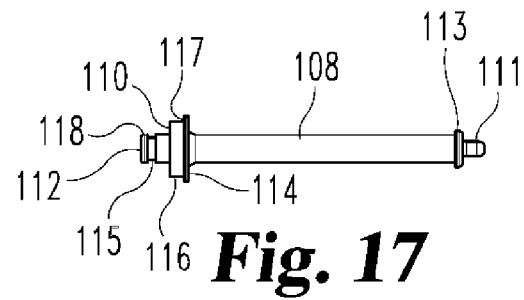
FIG. 17 is an enlarged view of a bracket mounting post.

The flexible brackets are configured to removably receive and hold the variety of instruments and devices positioned within the tray. For example, flexible bracket 56 (FIG. 5) includes a flexible web 69 integrally joined to a pair of cylindrical ends 67 and 68 each having a passage extending therethrough to removably receive a post 108. The top end of web 69 is provided with a recess or hole to removably receive and hold the particular instrument or device within the tray. The flexible casing forming ends 67 and 68 are slipped over and around post 108 so that the top and bottom of ends 67 and 68 (FIG. 5) rest adjacent enlarged portions 113 and 114 (FIG. 17). The bottom end of post 108 extends through the floor 35 and may be secured thereto by an external retaining clip. The top end of post 108 has a reduced diameter top end to fit into the holes of any cover or tray stacked atop the post. Bracket 70 has an upstanding wall having a solid surface against which the ends of tools 64 and 65 may abut.

Fixture posts 43, 106 & 107 are mounted to fixture 41 and bracket mounting posts 108 are positioned within fixture posts 107, button fasteners 53 are positioned in ends 52 of posts 43 and rigid brackets 55 and 70 are mounted to posts 43 so ends 46 of button fasteners 53 extend through the brackets. Tray 31 is then positioned atop the posts so ends 46, 109, and 112 of the posts and button fasteners extend through the floor of the inverted tray with the ends 46 and 112 then being secured to the floor by the fastening means previously described. Tray 31 is then removed from fixture 41 along with its posts 43, 106 and 107 and the flexible brackets are slipped onto posts 108.

Figure 7:
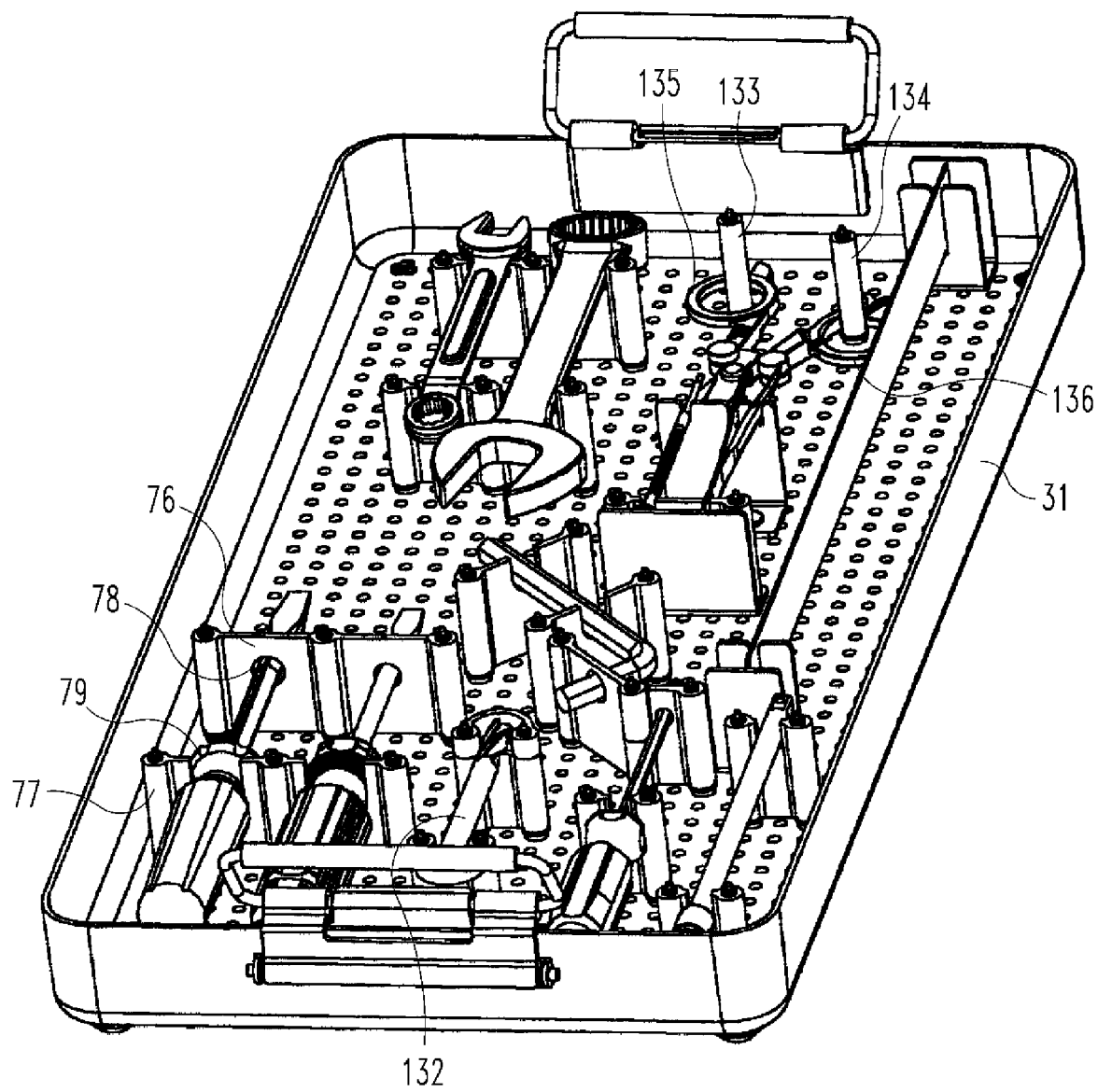
FIG. 7 is a top perspective view of an assembled tray having a variety of tools retained within with the tools shown being non-medical tools simply for illustration purposes only.

The flexible and rigid brackets are configured depending upon the instrument or device to be held within the tray. For example, flexible brackets 76 and 77 (FIG. 7) are mounted by vertical posts 108. Bracket 76 includes a hole 78 through which the shank of a screw driver extends whereas bracket 77 includes an upwardly opening recess to receive the handle 79 of the screw driver. Brackets 76 and 77 are designed to each receive three vertical posts thereby allowing for the mounting of a pair of screw drivers. The tools shown in FIG. 7 are for illustration purposes only.

The top end 111 of post 108 is extendable through the optional cover 32 (FIG. 1) or optional insert tray identical to and positioned above tray 31 thereby reinforcing the post and the surrounding floor and preventing any deformation by inertial forces generated by movement of the instruments and devices held within the tray. The top ends 111 of the posts extend through the holes of the cover limiting movement of the posts during any movement of the tray and also in the event medical instruments within the tray impact the posts.

Posts 108 extend from the floor 35 of tray 31 to cover 32 thereby allowing the ends 67 and 68 (FIG. 5) of the flexible brackets to extend with integral flexible web 69 from floor 35 to cover 32. Prior flexible brackets typically hold the various surgical instruments, implants and related devices in a press fit relationship since the brackets did not extend to the underside of the cover, preventing utilization of the cover for vertical retention. Concerns therefore exist relative to cleaning and sterilization issues existing between a tight fitting bracket relative to the device held by the bracket. The flexible brackets disclosed herein are produced from silicone and are supported along their entire height from floor to cover allowing the openings in the integral web 69 to loosely receive and hold the surgical instruments, implants and related devices providing for superior sterilization results. Further, the silicone brackets completely encase posts 108 preventing damage to the devices held by the brackets by preventing the devices from contacting the posts as compared to conventional brackets and metal posts not encased in silicone or other protective coatings.

Figure 10:
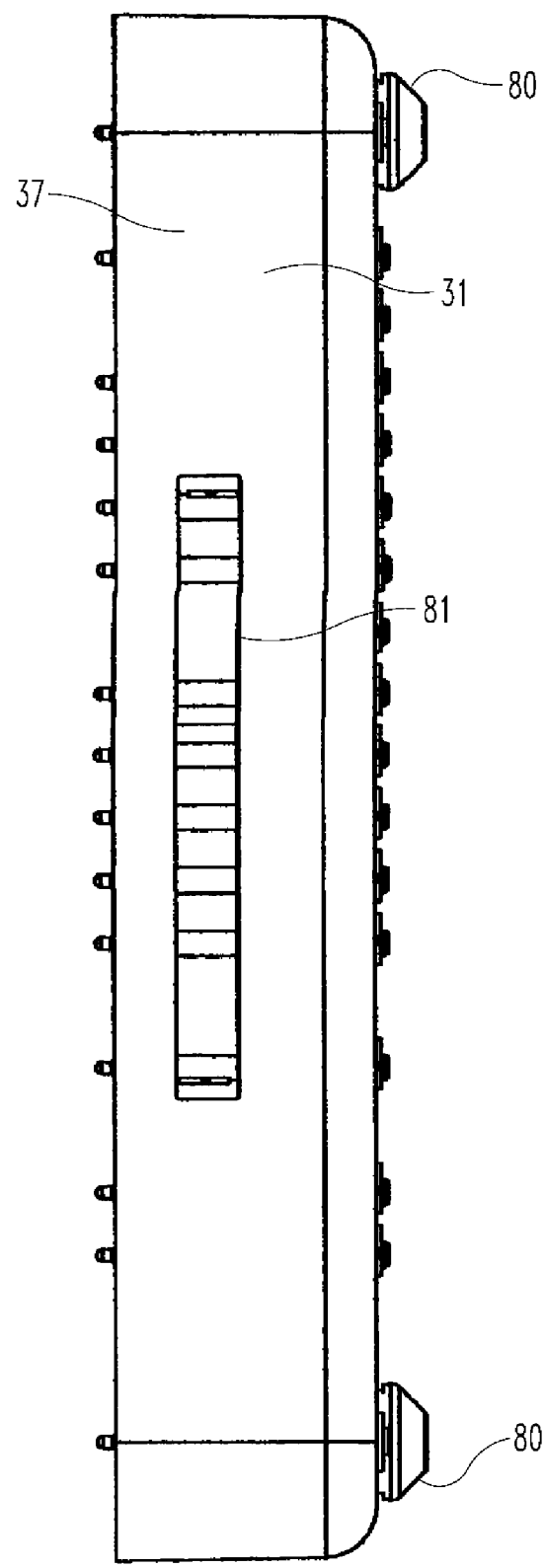
FIG. 10 is an enlarged end view of the tray of FIG. 5.

A plurality of external stacking feet 80 (FIG. 10) are provided on the under surface of tray 31. The stacking feet may be cast, machined or molded from any suitable material and serve to elevate the system when placed upon sterile drape used to cover work surfaces at the point of use. The feet 80 also serve to locate stacked systems atop one another by nesting within features present on the system cover 32. The general shape of each foot allows the system to be placed upon or removed from wire racks without snagging and presents soft contours minimizing the possibility of puncturing sterile wrap. The foot 80 is ideally fastened to the floor 35 of the container using the same retaining clip found elsewhere in the system, and may or may not contain features to allow placement of internal components in perforations adjacent to that in which the foot is affixed. The feet may be placed in any unoccupied perforation. At minimum, diagonally opposed feet are required for proper stacking. In the embodiment shown in FIG. 10, each foot 80 has a truncated conical shape with an upper pin (not shown) extending upwardly through the holes 52 of the bottom floor 35 of tray 31. The pins of the feet may then be secured to floor 35 by any suitable means, such as the retaining clips, threaded bolts or internally threaded nuts.

Handle assemblies 33 and 34 (FIG. 1) are attached to the opposite end walls of tray 31. End walls 36 and 37 have rectangular openings to facilitate the mounting of the assemblies.

Figure 11:
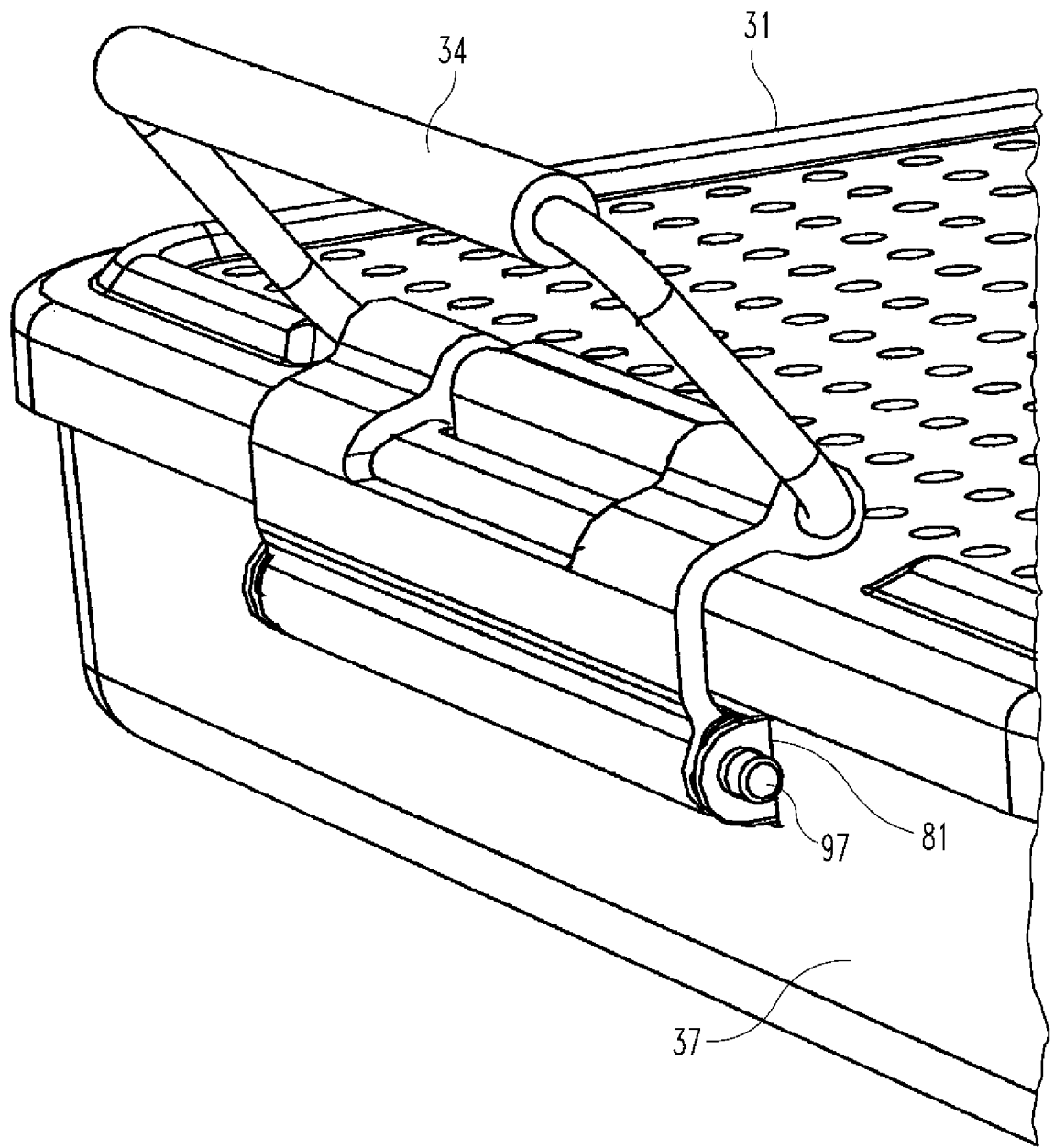
FIG. 11 is an enlarged fragmentary perspective view of one end of the tray including the cover and showing a handle mounted to the tray.
Figure 12:
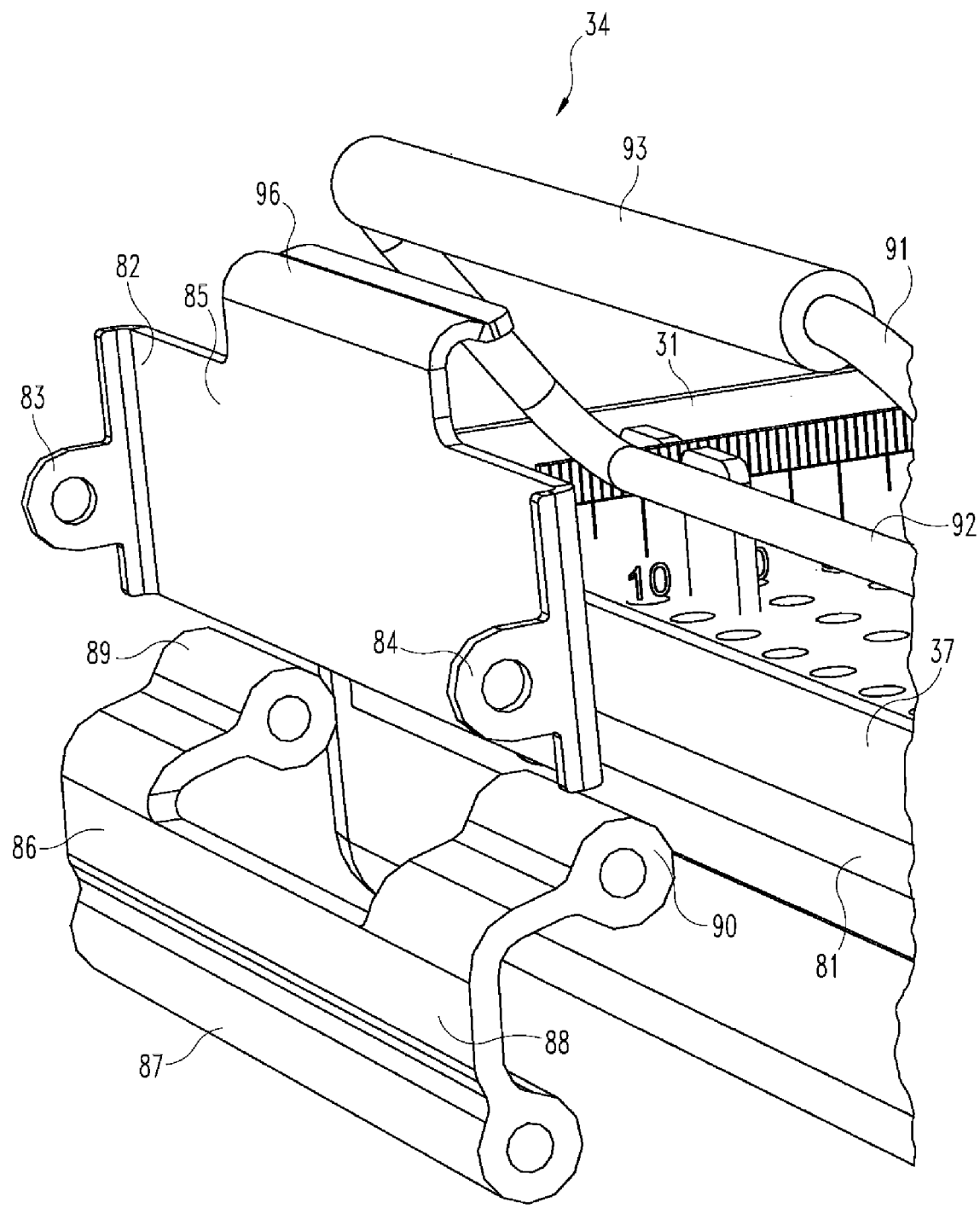
FIG. 12 is the same view as FIG. 11 only showing an exploded view of the handle with the tray assembly having the cover removed therefrom.

Assembly 34 will now be described it being understood that an identical description applies to assembly 33. Assembly 34 includes a folded sheet metal bracket 82 (FIG. 12) with a pair of ears 83 and 84 extending through rectangular opening 81 provided in wall 37. The main body 85 (FIG. 12) of bracket 82 is positioned immediately adjacent and inside wall 37. Bracket 82 has a hook shaped top end 96 that protrudes above the top of tray 31 and through the cover 32 when mounted to the tray. An elastomeric member 86, having a cross section identical to the flexible bracket 56, is mounted to bracket 82 by means of a cylindrical pin 97 (FIG. 11) that extends through ears 83 and 84 and the hollow cylindrical bottom end 87 of member 86. Member 86 has a central web 88 integral with end 87. Retaining clips similar to those used to affix the internal components to the tray floor also serve to retain pin 97 to ears 83 and 84. The clips reside in grooves on pin 97 located between the elastomeric member 86 and ears 83 and 84. It is understood that flexible bracket 56 and elastomeric member 86 are the same raw material.

A wire bail forms a handle 91 with the lower wire portion 92 of the wire bail 91 extending through the hollow centers of top ends 89 and 90 of elastomeric member 86. A tubular grip 93 receives the top opposite spaced apart ends of handle 91 and acts to cushion the gripping area of the handle assembly.

When assembly 34 is in a non-latch position, ends 89 and 90 are located vertically above web 88 and bottom end 87. Web 88 assumes the bent configuration depicted in FIGS. 11 and 12 when assembly 34 is pulled inwardly so that the bottom wire portion 92 of the handle 91 that extends through ends 89 and 90 may be retained securely beneath the hook shaped top end 96 of bracket 82. By pulling the wire bail inwardly, the elastomeric member 86 is stretched so that the wire bail bottom portion 92 may be retained securely beneath the hook shaped top end 96. Thus, the weight of the system is not carried by the elastomeric member 86 but by the bracket 82 and thus by the tray. Accidental disengagement of the wire bail handle from the hook will not result in dropping of the system and its contents. Cylindrical bottom end 87 is positioned adjacent and outwardly of wall 37. Web 88 attaches cylindrical bottom end 87 to the pair of cylindrical hollow top ends 89 and 90 that are positioned over tray 31. Ends 89 and 90 are spaced apart with hook shaped end 96 of bracket 82 positioned therebetween.

Figure 13:
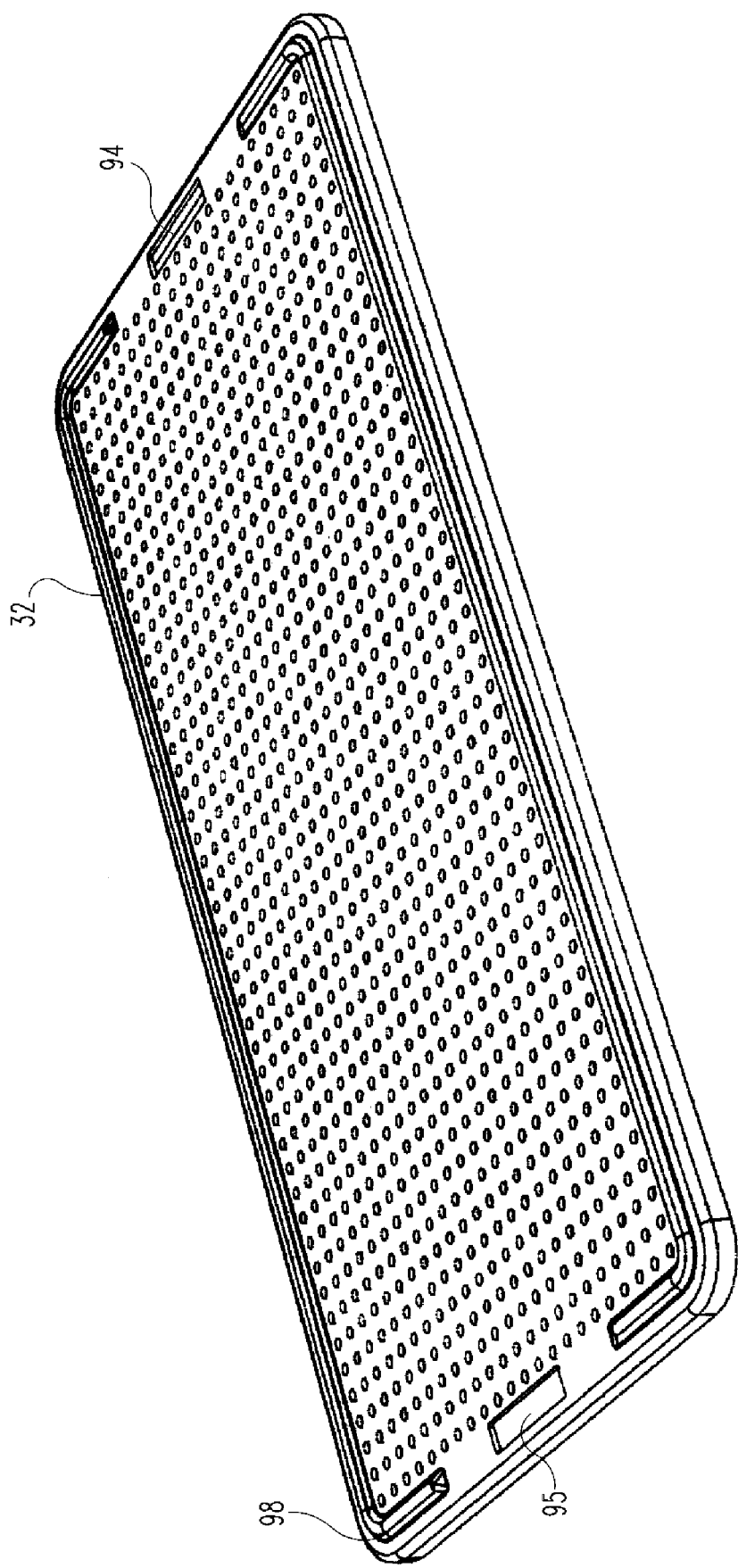
FIG. 13 is a perspective view of the cover.
Figure 14:
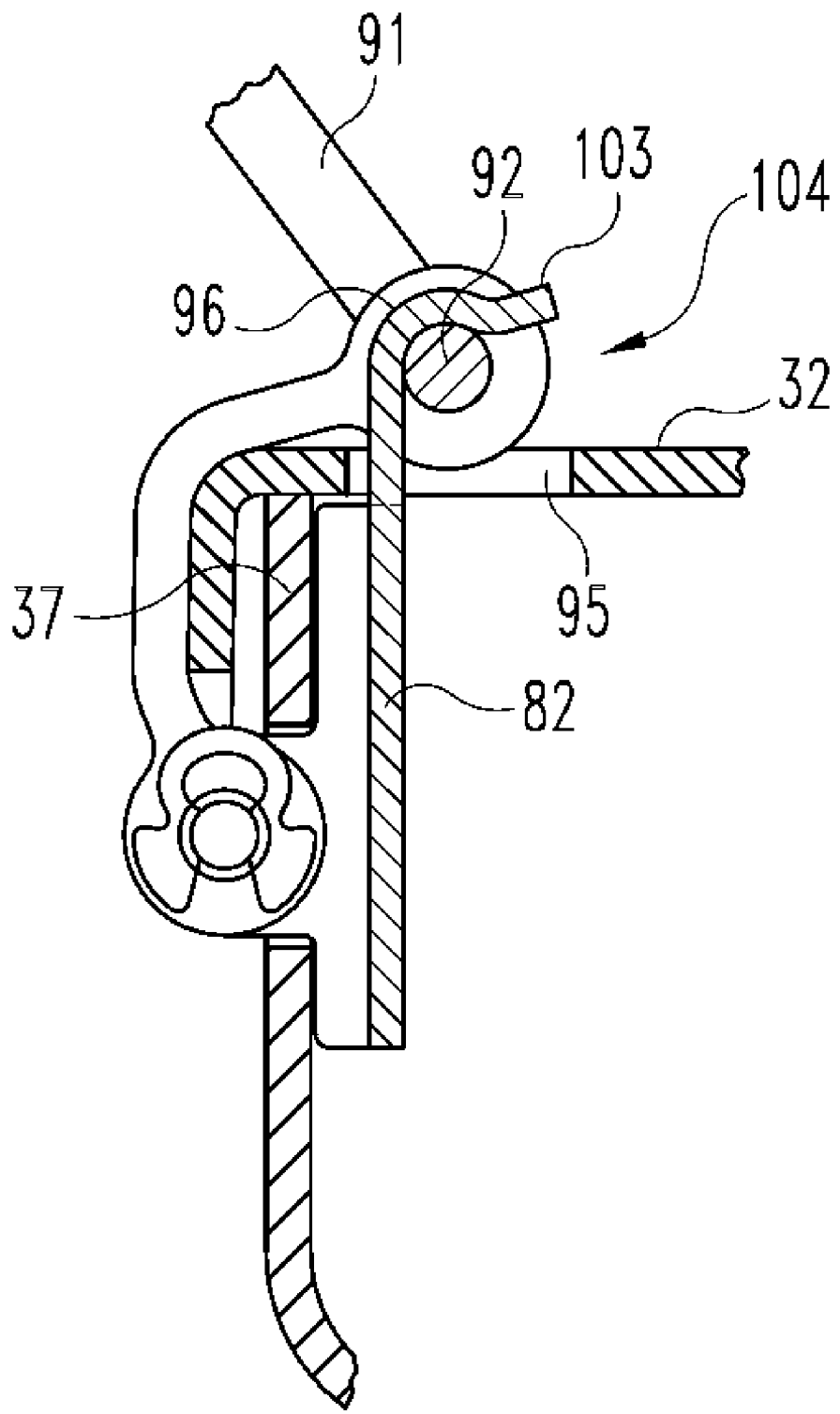
FIG. 14 is a fragmentary cross-sectional view illustrating the cover mounted to the tray with a hook-shaped end protruding through the cover and the handle positioned between the hook-shaped end and the cover.

Cover 32 may be constructed from any sterilizable, suitably rigid material. For example, the cover may be a drawn aluminum pan, fabricated from folded sheet metal or from polymer resin being molded, vacuum formed etc. The quantity and locations of perforations present in the cover must, at a minimum, match exactly those present for the fastening of internal components to the floor of a single layer system or the floor of the top insert tray in a multiple layer system. Cover 32 (FIG. 13) includes a pair of rectangular openings 94 and 95 at the opposite end portions to allow for the passage of hook shaped ends 96 of assemblies 33 and 34.

The cover is mounted to the tray when using sterile wrap in lieu of rigid container systems, as the cover is necessary to prevent the contents of the container from escaping their retaining brackets when the system is tumbled during the wrapping process.

When installing the cover to the tray, ends 111 of the posts 108 are extended into or through the cover. Hook shaped ends 96 are extended from beneath the cover through openings 94 and 95 (FIG. 13) with the hook shaped ends then protruding over and above the cover. The holes extending through the cover and floor allow fluid sterilant flow facilitating the sterilization of the items held within the tray.

Tubular grips 93 of assemblies 33 and 34 are then grasped and pulled upwardly and then over the cover positioning bottom wire portion 92 of each handle around the edge 103 of hook shaped end 96 in the direction of arrow 104 and into and beneath the hook shaped end so that portion 92 is positioned between the hook shaped end 96 and the top of the cover. In the event the cover is not utilized, then wire portion 92 is still positioned beneath the hook shaped end 96.

With the cover mounted to the tray, the handles may rotate approximately 210 degrees from a position lying inward and flush atop the cover to a binding position extending outward of the perimeter of the cover. This binding position, achievable by carrying the system by the handles while inverted, increases the security that the handle assemblies will remain engaged in the retained cover position. The method of carrying the system with or without the cover present and securing the cover when present is equally applicable to any container system of suitably rigid material having a close or flush fitting cover and appropriate openings at each end of the floor and cover. Additional characteristics include: (1) a latched or unlatched state is visually apparent, (2) one-hundred percent field repairable without the use of special tools, and (3) the system does not require precision manufacturing tolerances for optimum function.

By removing the cover from the tray, the system is properly configured when used inside present rigid container systems in lieu of sterile wrap systems. With the perforated cover mounted to the tray, the system is configured when using sterile wrap as the cover is necessary to prevent the contents of the container from escaping their retaining brackets when the system is tumbled during the wrapping process.

Cover 32 (FIG. 13) may be provided with circumferentially extending ridges 98 or other projections to promote the secure stacking of the systems by providing nesting locations for the external feet 80 when the systems are placed atop one another.

Many variations of the described structure are contemplated and included in the present invention. For example, the flexible and rigid brackets may take many shapes and configurations depending on the items to be secured. As an example, flexible bracket 130 (FIG. 5) includes a bowed web 131 integral with the opposite tubular shaped ends forming a pouch to receive the end of an instrument 132 (FIG. 7). Further as an example, spaced apart posts 133 and (FIG. 7) include an outer silicone casing extending around posts 108 to receive the ring shaped ends 135 and 136 (FIG. 7) of an instrument.

When mounting the various surgical instruments, implants and devices in the tray, it is helpful for the user to know where the particular device is to be mounted within the tray. Thus, we have provided labels associated with the flexible and rigid brackets. The labels may consist of a flat plate 140 (FIG. 20) made from a metal, plastic or paper material and having the indicia 141 provided on the upwardly facing surface of the label identifying the particular device to be mounted to the bracket. The indicia may consist of a bar code, letters or numbers or any type of identifying marks. The indicia may be placed on the plate by printing, etching or any conventional technique. The thickness of the plate is such that the ends of the plate fit between the floor 35 of the tray and the head of button fastener 53 and between the floor 35 of the tray and shoulder 117 (FIG. 17) of bracket mounting post 108. The thickness of plate 140 may be equal to the length of reduced portion 116 of post 108. Thus, the labels may be utilized with the rigid brackets and/or flexible brackets previously described.

Figure 21:
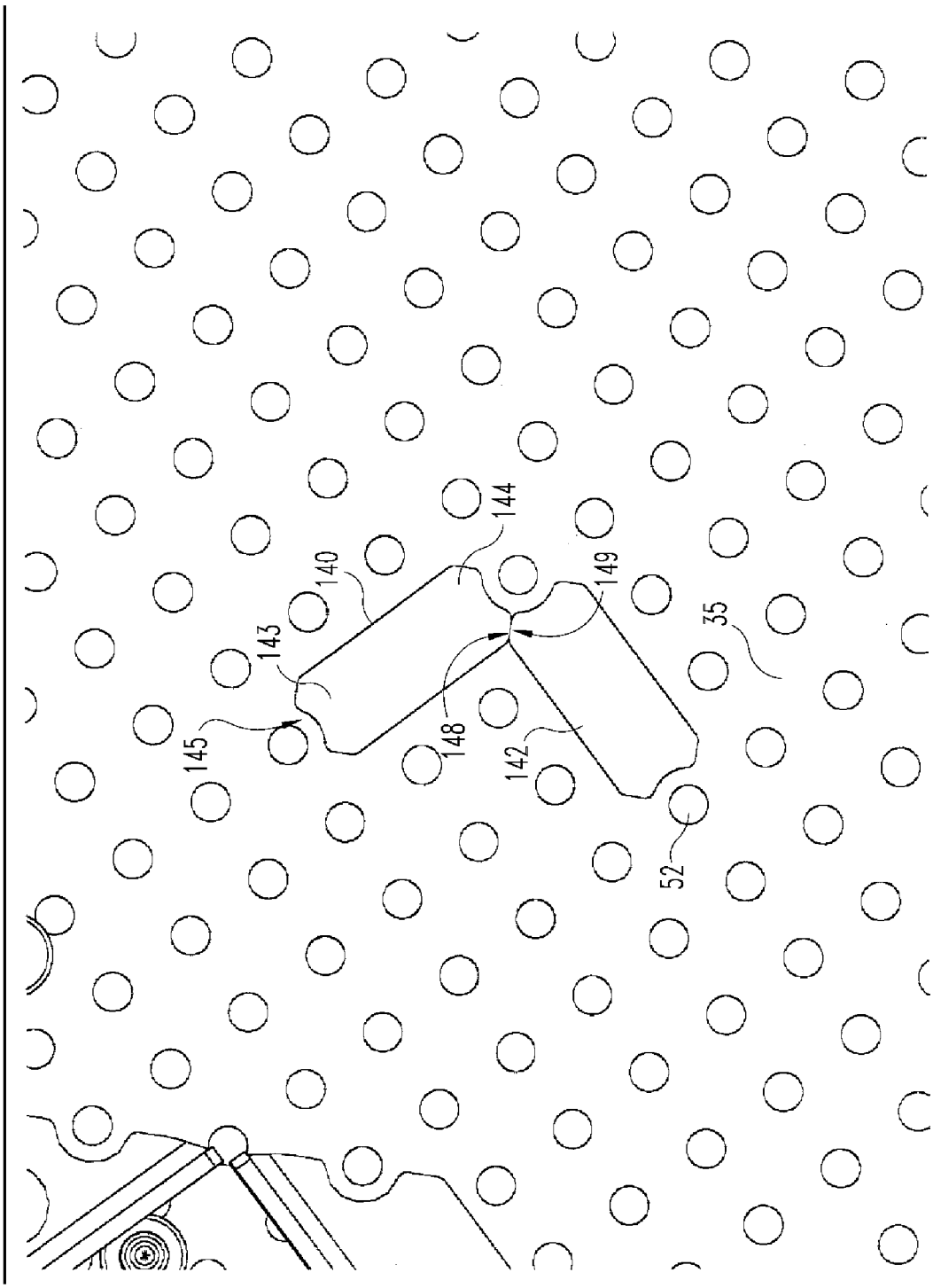
FIG. 21 is a top view of two of the labels illustrated in FIG. 20 with the bracket and, mounting posts and button fastener removed.

Label plate 140 has a pair of opposite beveled ends 143 and 144 (FIG. 21) with a curved recess 145 to partially receive the shank of button fastener 53 and post 108. The width 146 of plate 140 equals the distance 147 between the centers of adjacent holes 52 of floor 35 to allow positioning of adjacent plates extending between rows of adjacent holes 52. Plate 142 is shown positioned beneath a flexible bracket 56 and extending out from either side of the flexible web of the bracket to allow label indicia to be provided on the label to show on the opposite sides of the flexible web. The beveled edges 148 and 149 of labels 140 and 142 allow locating the labels and brackets at right angles relative to each other thereby allowing for a wide variety of positioning of the brackets atop the floor.

Figure 20:
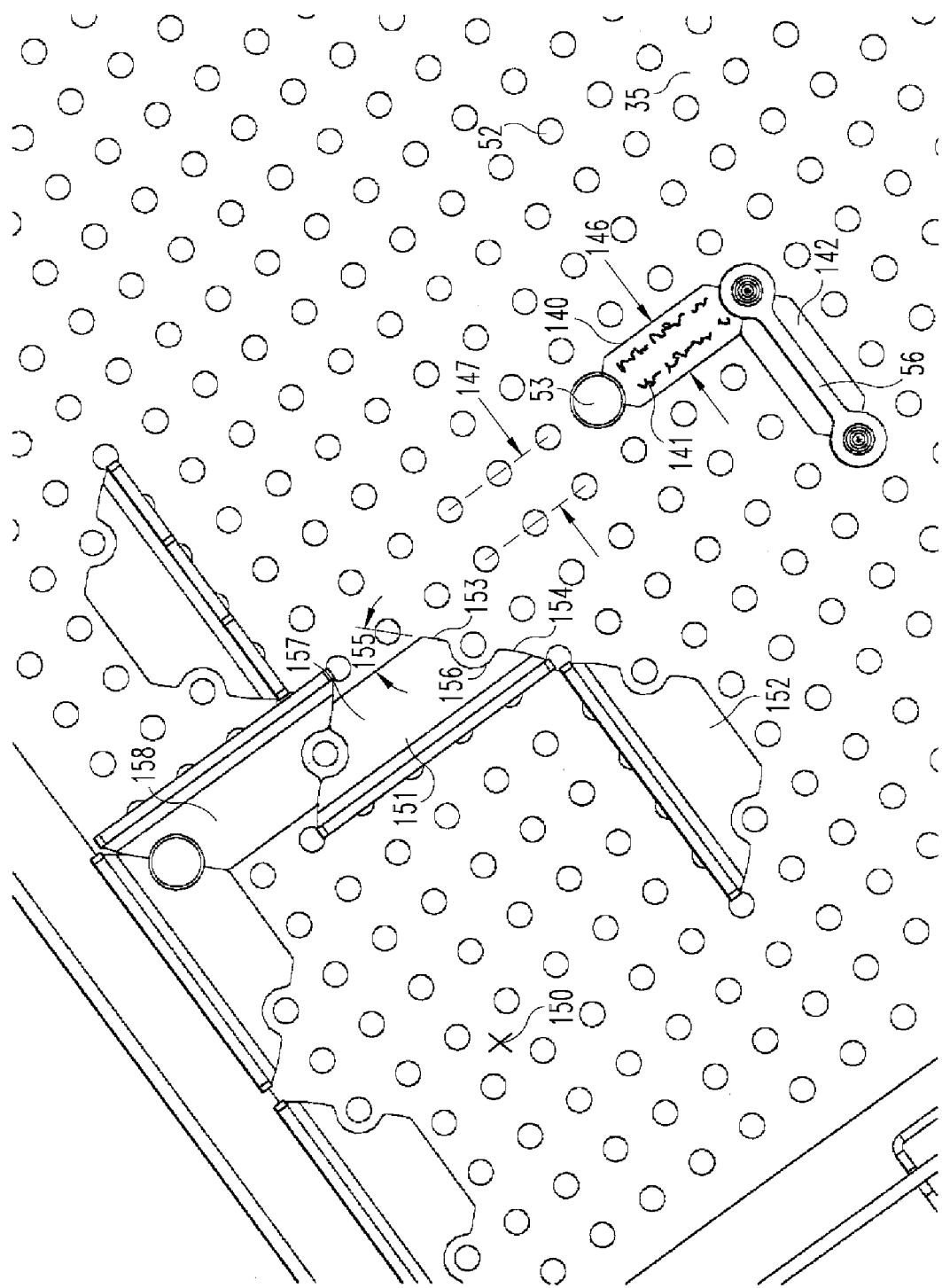
FIG. 20 is an enlarged fragmentary top view of the tray illustrating labels positioned beneath rigid and flexible brackets as well as an alternate embodiment of the rigid bracket.

A variation of the rigid bracket is shown in FIG. 20. Brackets 151 and 152 are identical to brackets 55 and 70 previously described except that the opposite end edges of the wall 157 resting atop floor 35 are formed at forty-five degree angles 155 relative to the bracket longitudinal axis extending the length of the bracket creating at the opposite ends of each bracket a pair of edges 154 and 153 between which is formed curved recess 156 to receive the shank of the button fastener 53. Edges 154 and 153 may also be in contact with the beveled end edges of the labels. For example, a label 140 having edge 149 may be positioned so edge 149 contacts edge 153 of bracket 151 with a fastener 53 then securing label 140 to the tray floor. Thus, the labels may be utilized with both rigid brackets and flexible brackets. Some of the button fasteners are removed in FIG. 20 from the brackets to illustrate the bracket edges. A pair of brackets 151 and 158 may be aligned in a row with their end edges in contact with each minimizing the space occupied by adjacent brackets. The brackets may be arranged to form areas or compartments, for example area 150, in which are located specific types of items to be held by the brackets.

Figure 22:
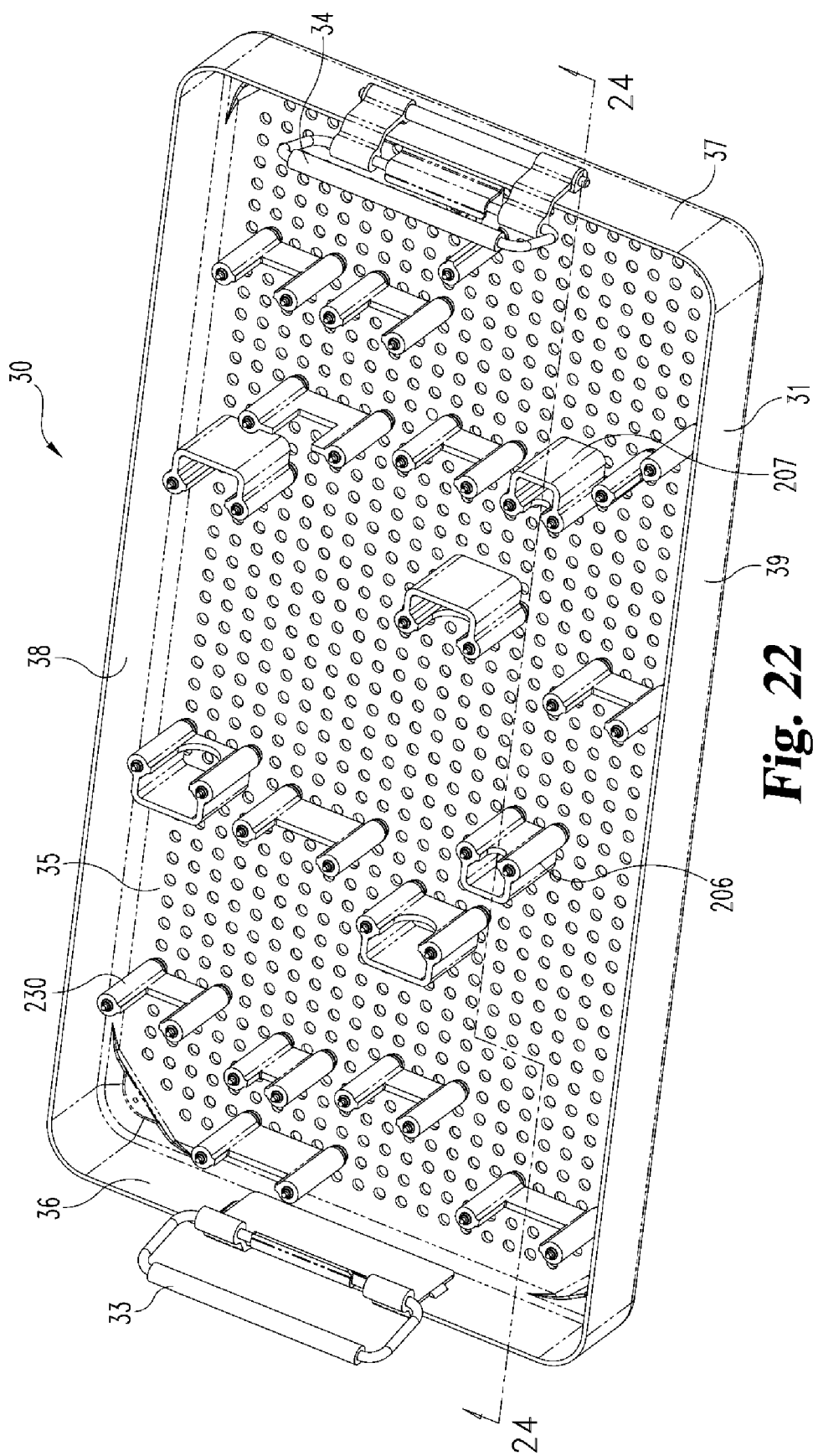
FIG. 22 is a perspective view of the preferred embodiment of the tray having flexible brackets and posts incorporating the present invention.
Figure 23:
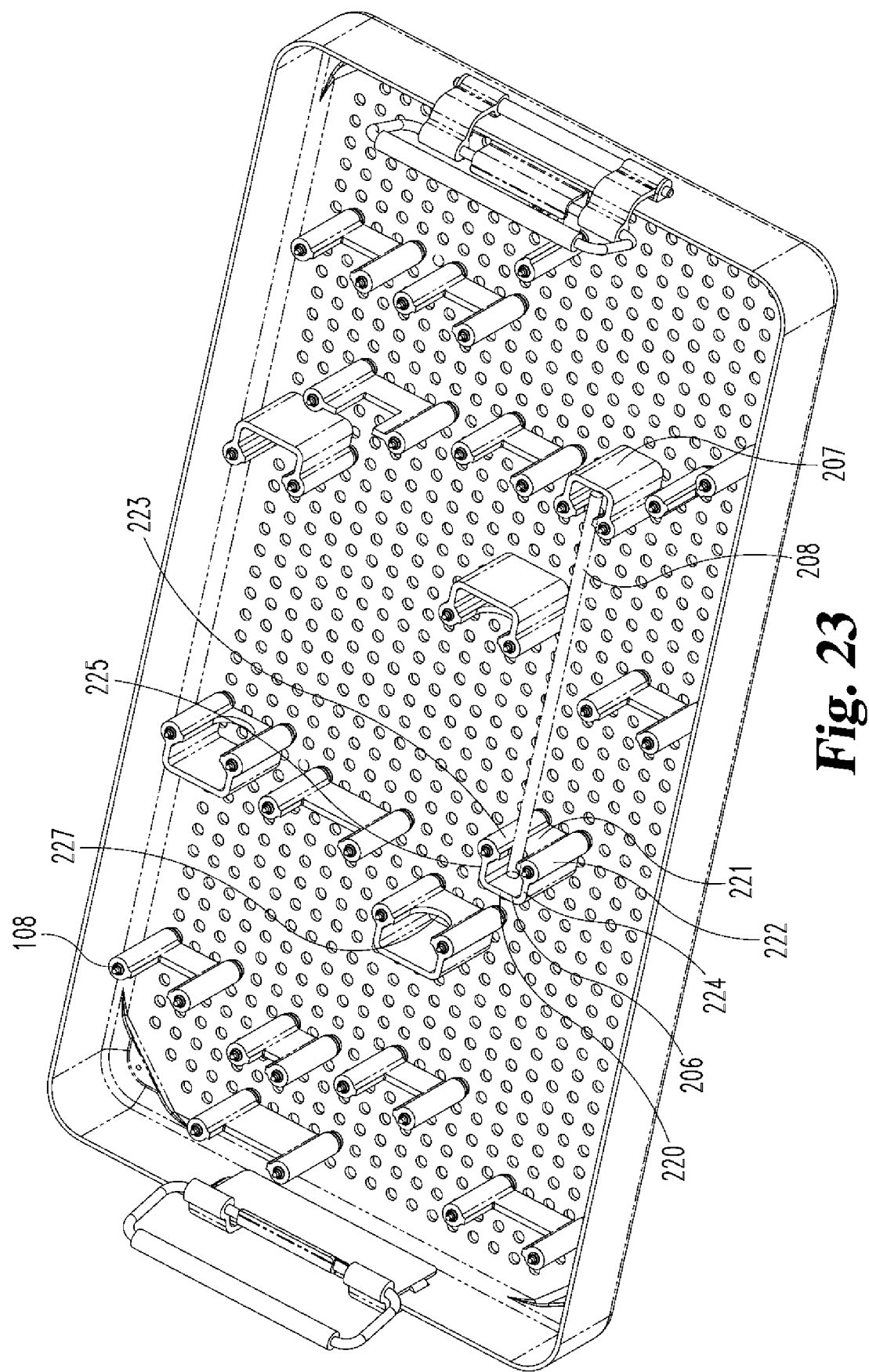
FIG. 23 is the same view as FIG. 22 only showing two of the flexible brackets holding a medical instrument or other type of item.

The container and tray shown in FIGS. 22-28 is identical to the previously described tray and cover of FIGS. 1-21 with the exception that additional flexible brackets are illustrated, the bottom surface of the cover includes spacers extending thereacross to provide a cushion in the event the instruments within the container move towards the cover, a template plate is mounted to the tray floor, and the tray feet are integral with the floor. Thus, container 30 (FIG. 22) includes a tray 31 and cover 32 (FIG. 28) removably secured thereto by a pair of handle assemblies 33 and 34 (FIG. 22). The tray has a perforated floor 35 integrally joined to a pair of end walls 36 and 37 and a pair of side walls 38 and 39 with the end walls and side walls extending outwardly and upwardly from the floor forming a cavity into which may be located surgical implants, implants and related devices.

Cover 32 includes a pair of downwardly extending end walls 209 and 210 (FIG. 27) that fit externally against the end walls 36 and 37 of the tray. Likewise, the cover includes a pair of downwardly turned side walls 211 and 212 (FIG. 28) that extend externally and adjacent the side walls 38 and 39 (FIG. 22) of the tray. A pair of slots 213 and 214 (FIG. 28) are provided adjacent the end walls of the cover to allow the hook shaped ends 96 to extend therethrough as previously described and illustrated in FIG. 12. A plurality of cushion spacers 215 are provided on the downwardly facing inside surface of cover 32 to limit movement of any instruments held within the tray as the tray is tumbled thereby preventing contact between the instruments and the main body of cover 32 and protect the surface finish of the instruments and the cover. A variety of insulation spacers 215 may be provided. For example, in FIG. 28 there are shown a plurality of diagonally extending spacers 215 positioned between the holes extending through the cover. Excellent results have been obtained by placing a bead of silicone with the bead extending diagonally across the cover. Once the silicone has solidified, the insulation spacers are formed. The present invention contemplates and includes utilization of different types of materials to form spacers 215 such as, various plastics and rubbers. Likewise, spacers 215 do not need to extend diagonally and continuously across the cover but may extend at different angles and may be interrupted as the spacers extend across the cover.

In lieu of utilizing feet 80 (FIG. 10) secured to the bottom of the tray which nest in complimentary shaped recesses of the cover, the present invention contemplates and includes downwardly extending feet 216 (FIG. 27) integral with the bottom wall 35 and end and side walls of the tray. Likewise, the cover 32 (FIG. 28) may be provided with downwardly extending depressions 217 (FIG. 27) to nestingly receive feet 216 when the containers are vertically stacked. Recesses 217 are formed immediately inward of the upraised corners 218 (FIG. 27) of the cover whereas feet 216 are located inwardly from the end and side walls of the tray thereby being aligned with recesses 217.

In lieu of using the flat plates 140 (FIG. 20) which are provided with indicia identifying the particular instrument or device to be mounted to the brackets, a removable large indicia plate 200 (FIG. 25) is mounted within the tray. The plate is provided with images, graphics and/or outlines 205 (FIG. 26) on the top surface thereof corresponding to the particular instrument to be mounted to the brackets, in turn, mounted to the tray atop plate 200.

As previously explained, mounting posts 108 (FIG. 17) have opposite ends 111 and 112 sized to fit respectively through the holes in cover 32 and the perforated floor 35. Post 108 has an enlarged portion 114 having a diameter larger than the cylindrical main body of post 108 thereby forming an upwardly facing surface 219 (FIG. 24) upon which plate 200 rests. Plate 200 is spaced upwardly from the bottom floor 35 of the tray and has two recesses 201 and 202 (FIG. 25) to allow the plate to be moved downwardly past the opposing handles secured to the opposite end walls of the tray when being mounted to the floor of the tray. Since plate 200 is spaced apart from the floor, the space in between may be easily cleaned and the flow of sterilant in the space is not impeded. The holes 203 of plate 200 are sized to allow enlarged portion 113 and the main body of post 108 to extend therethrough but are not sufficiently large to allow the enlarged portion 114 to be extended through the holes. Immediately, beneath enlarged portion 114 is a reduced portion 116 having a reduced diameter as compared to enlarged portion 114. Reduced portion 114 forms a downwardly facing shoulder 110 (FIG. 17) that abuts against the upwardly facing surface of floor 35 thereby cooperatively with the retaining ring on the opposite side of the tray floor holding the post in an upright and fixed position and spacing plate 200 from the floor. Plate 200 may extend across the entire width and length of the floor or only across a portion thereof depending on the positioning of the instruments within the tray.

A plurality of flexible brackets are mounted to the tray by posts 108. In the embodiment shown in FIG. 23, a pair of flexible brackets 206 and 207 are depicted removably holding a medical instrument 208. Bracket 206 will now be described it being understood that an identical description applies to bracket 207. Flexible bracket 206 is produced from a material, such as, silicone or other material that exhibits flexibility. Bracket 206 includes a pair of parallel walls 220 and 221 that are spaced apart and are integrally joined to a pair of flexible upstanding tubes 222 and 223. Wall 220 has a c-shaped configuration and includes a pair of legs 224 and 225 integrally joined together at one end of the legs and with the opposite ends of the legs integrally joined to tubes 222 and 223. Walls 221 has a C shaped configuration and extend across the gap between one tube 222 to the other tube 223 without having any bends in the wall.

Figure 24:
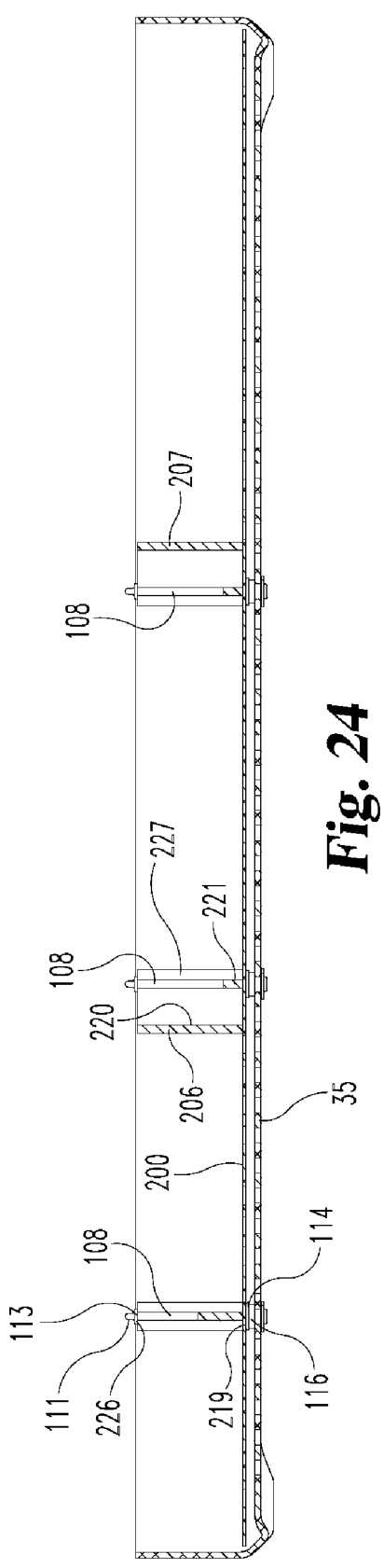
FIG. 24 is a cross-sectional view taken along the line 24-24 of FIG. 22 and viewed in the direction of the arrows and showing the template plate of FIG. 25 mounted to the tray.
Figure 27:
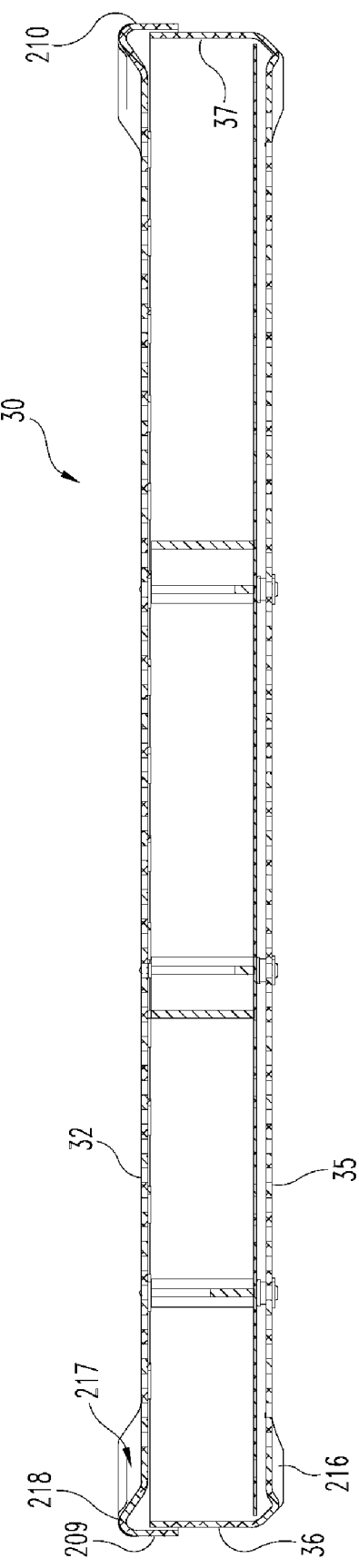
FIG. 27 is the same view as FIG. 24 only showing the cover mounted to the tray.
Figure 25:
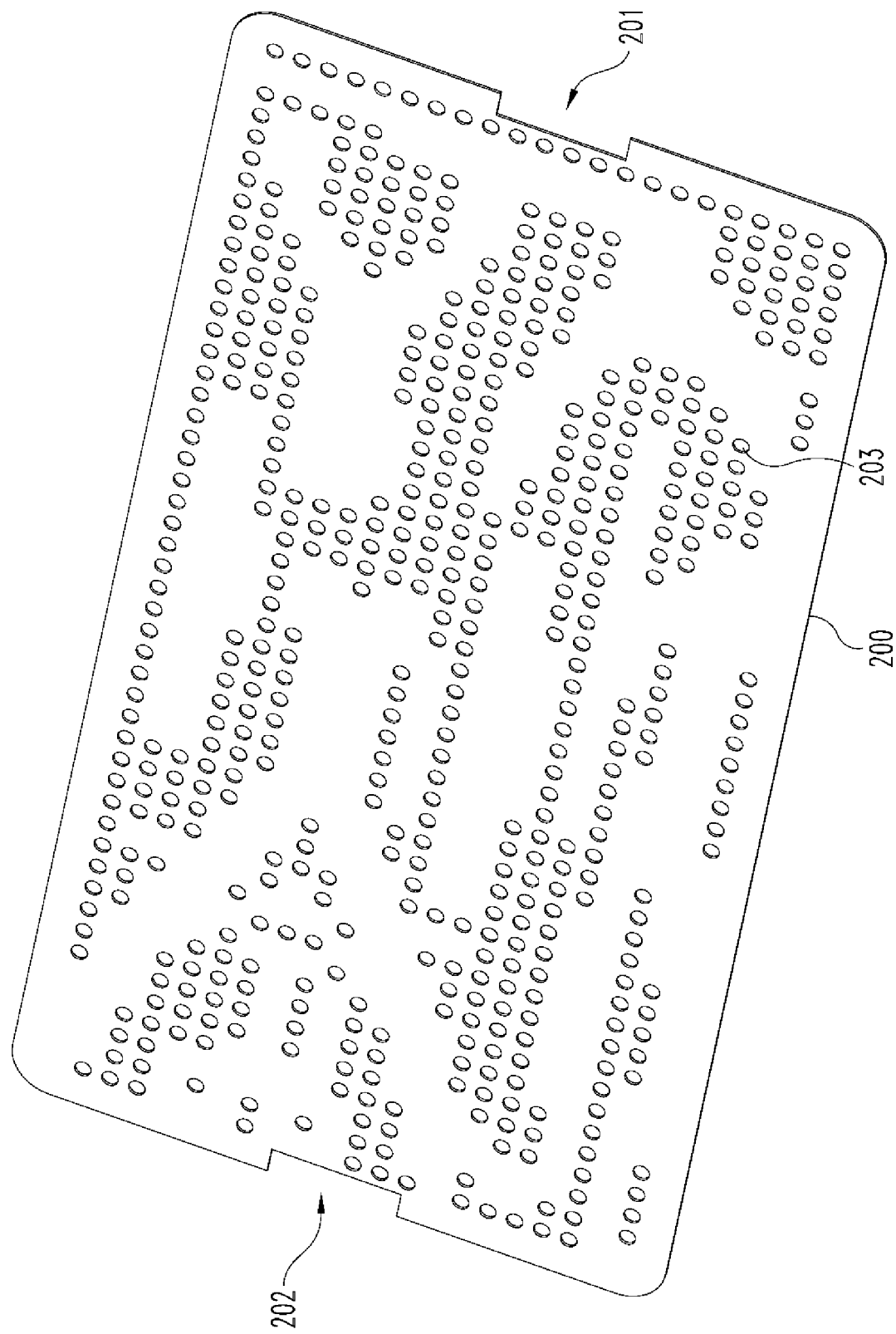
FIG. 25 is a top perspective view of a template plate mountable atop the floor of the tray of FIG. 22.
Figure 26:
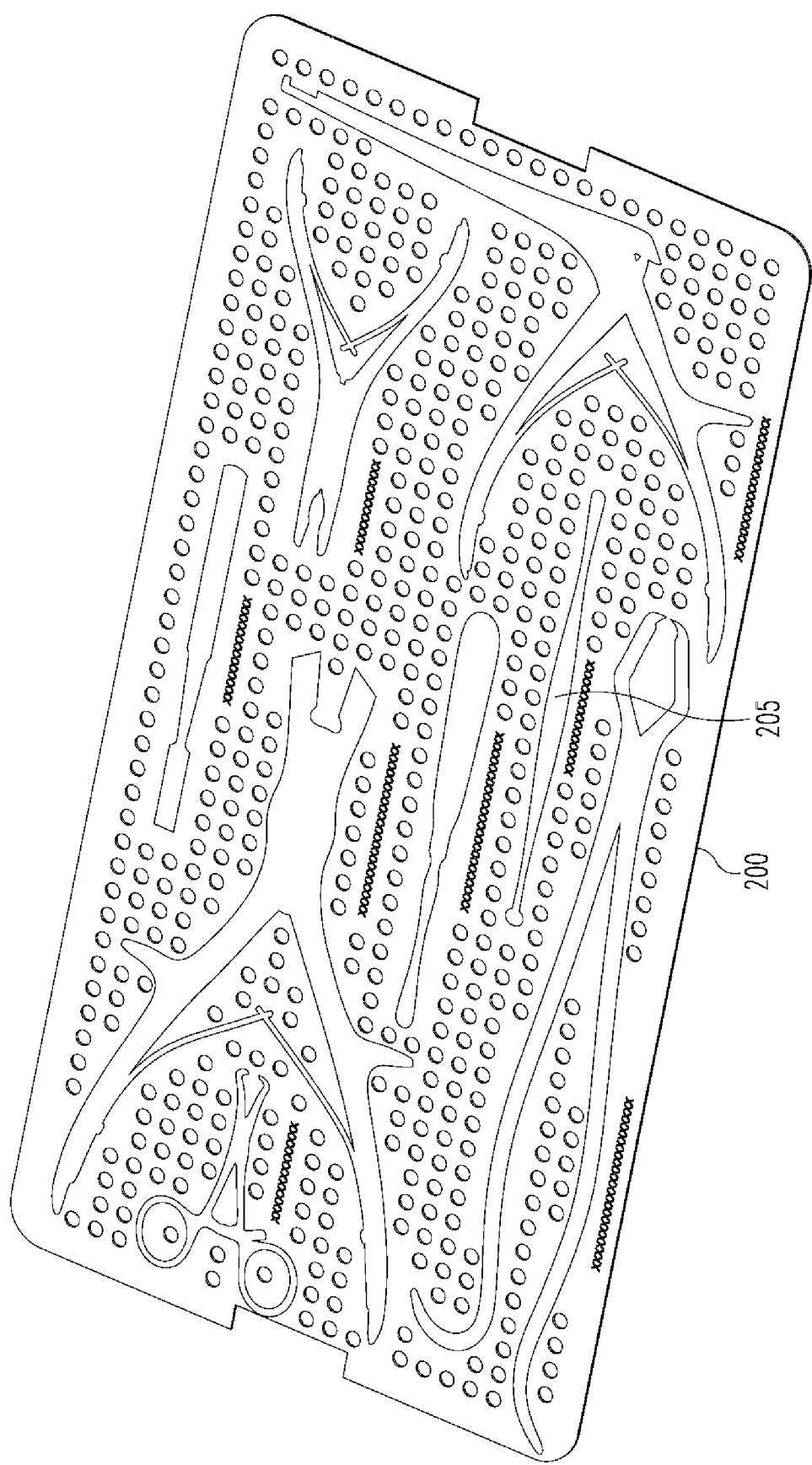
FIG. 26 is the same view as FIG. 25 only showing location indicia marked on the template plate.
Figure 28:
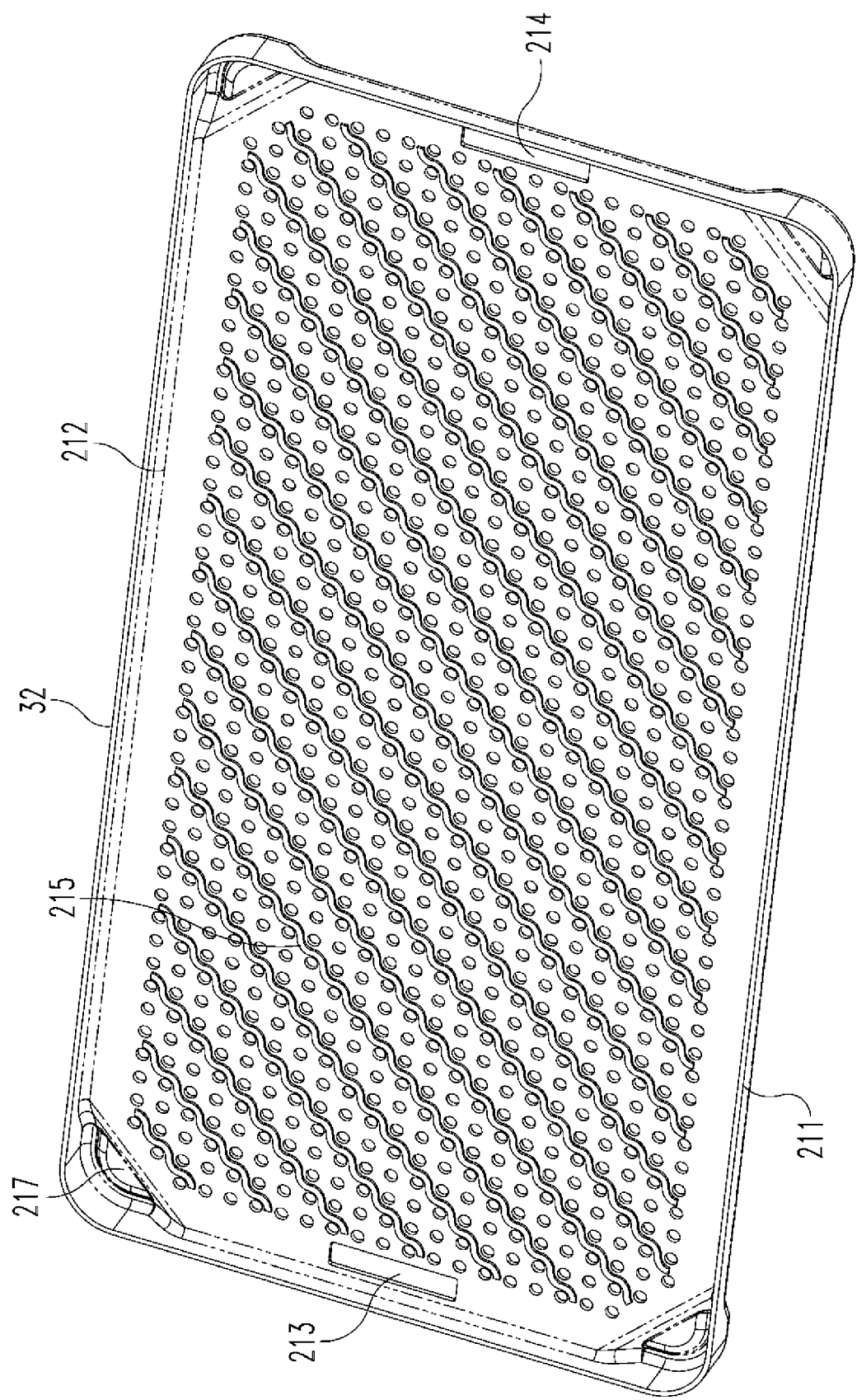
FIG. 28 is a bottom perspective view at the cover mountable to the tray of FIG. 22.

Tubes 222 and 223 are hollow to slidingly receive posts 108 with the bottom end of the tubes resting atop plate 200 which rests atop upwardly facing surfaces 219 (FIG. 24) of the enlarged portions 114 of the posts and with the top ends of the tubes abutting against the downwardly facing surfaces 226 of the enlarged portions 113 of the posts. Thus, tubes 222 and 223 are held between and by the enlarged portions 113 and 114. In the embodiment shown in FIG. 23, the tray is not provided with an indicia plate 200 and thus tubes 222 and 223 rest atop the upwardly facing surfaces 219 of the enlarged portions 114 of the two posts. On the other hand, FIG. 24 illustrates a tray having the removable indicia plate 200 mounted therein.

Wall 221 is provided with a cutout portion or recess 227 (FIG. 23) to receive one end of the instrument held therein. The size of the recess 227 is appropriate to releasably hold the instrument. Wall 220 extends from the bottom ends of the tubes 222 and 223 to the top ends of both tubes to provide a backup wall to limit movement of the instrument. Brackets 206 and 207 have walls 221 facing each other, with each having a recess portion to receive the opposite ends of the medical instrument.

Referring to FIG. 22, the tray is shown as having two different types of brackets. Some of the brackets are double walled brackets. For example, brackets 206 and 207 have a pair of spaced apart walls that span the gap between the upright tubes mounted to the tubes. That is, bracket 206 includes spaced apart walls 220 and 221 integrally joined to tubes 222 and 223. Both walls and tubes are provided from flexible material. A second type of bracket 230 includes a pair of upright flexible tubes mounted to the tray by the posts with a single wall spanning the gap between the tubes. Both the tubes and the single wall are produced from a flexible material. A particular advantage of all of the flexible brackets shown in FIG. 22 is that they may be extruded and then cut to the particular height desired. Wall 221 may be cut further thereby forming the hollow portion or recess 227. Excellent results have been achieved by producing both types of brackets from silicone.

Figure 18:
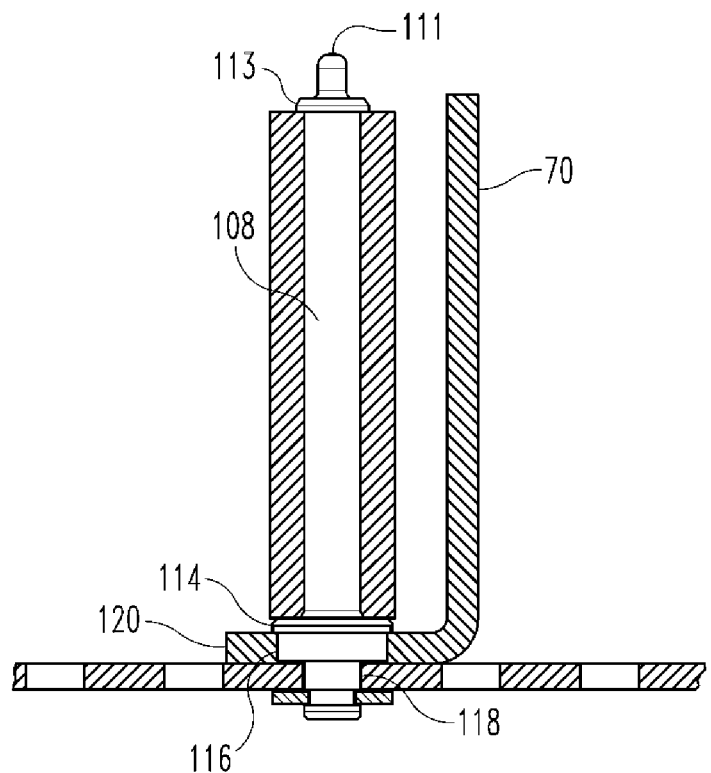
FIG. 18 is a cross sectional view taken along the line 18-18 of FIG. 6 and viewed in the direction of the arrows.

Post 108 is particularly advantageous in that the post may be used to extend through the bottom rigid wall 120 (FIG. 18) of rigid bracket 70 with wall 120 mounted in contact with the floor of the tray and surface 117 (FIG. 17) of enlarged portion 114. The upright flexible brackets, such as, bracket 230 (FIG. 22) may then be mounted atop the enlarged portion of the post as shown in FIG. 18 with the same combination also shown in FIG. 5 as flexible bracket 56 and rigid bracket 70. In such a case, indicia plate 200 is not utilized. Thus, wall 120 contacts the downwardly facing surface 117 of post 108 whereas the flexible bracket is mounted atop surface 219 (FIG. 24). In the event the indicia plate 200 is utilized, the indicia plate is positioned atop seat or surface 219 with the flexible bracket then being positioned in contact with the upwardly facing surface of indicia plate 200.

The preferred embodiment of the bracket utilized in the tray or container is shown in FIGS. 29-34. Bracket device 300 includes a bar or plate 301 produced from an extruded flexible material, such as silicone rubber. Bar 301 is held along its bottom portion by a pair of opposing brackets 303 and 304 that are removably mounted to a plate or base wall 302 that may be separate from the floor of a container or may be the actual floor of the container itself. The bar may be formed by extruding the flexible material along the length as contrasted to the height. For example, flexible bracket 56 (FIG. 5) is extruded in a direction that extends from the bottom of the bracket mounted adjacent the floor of the container to the top of the bracket whereas bar 301 is extruded in the direction from one end of the bar through its length 305 to the opposite end of the bar.

In the embodiment shown in the drawings, plate 302 includes four rows of holes extending therethrough with the rows extending the length of the plate. The holes are aligned across the width of the plate to enable the feet of brackets 303 and 304 to extend therethrough. Brackets 303 and 304 are rigid being produced from metal. The present invention contemplates and includes a plate with a different hole arrangement than that shown in FIG. 29.

Bracket 304 will now being described it being understood that a similar description applies to bracket 303. Bracket 304 (FIG. 30) includes a main body 306 with a plurality of downwardly extending legs 307 integrally attached thereto. Main body 306 has an outwardly facing surface 308 (FIG. 31) and inwardly facing surface 312. Each leg 307 has a top surface 310 and a bottom surface 311. The main body 306 is arranged relative to legs 307 at an acute angle 322 so that when the upwardly facing surface 310 is parallel to plate 302, main body 306 is arranged at an acute angle relative to the plate. That is, angle 322 formed between surfaces 310 and 312 is an acute angle. The plate shaped main body of brackets 303 and 304 are positionable to be parallel when mounted to the base wall.

Figure 30:
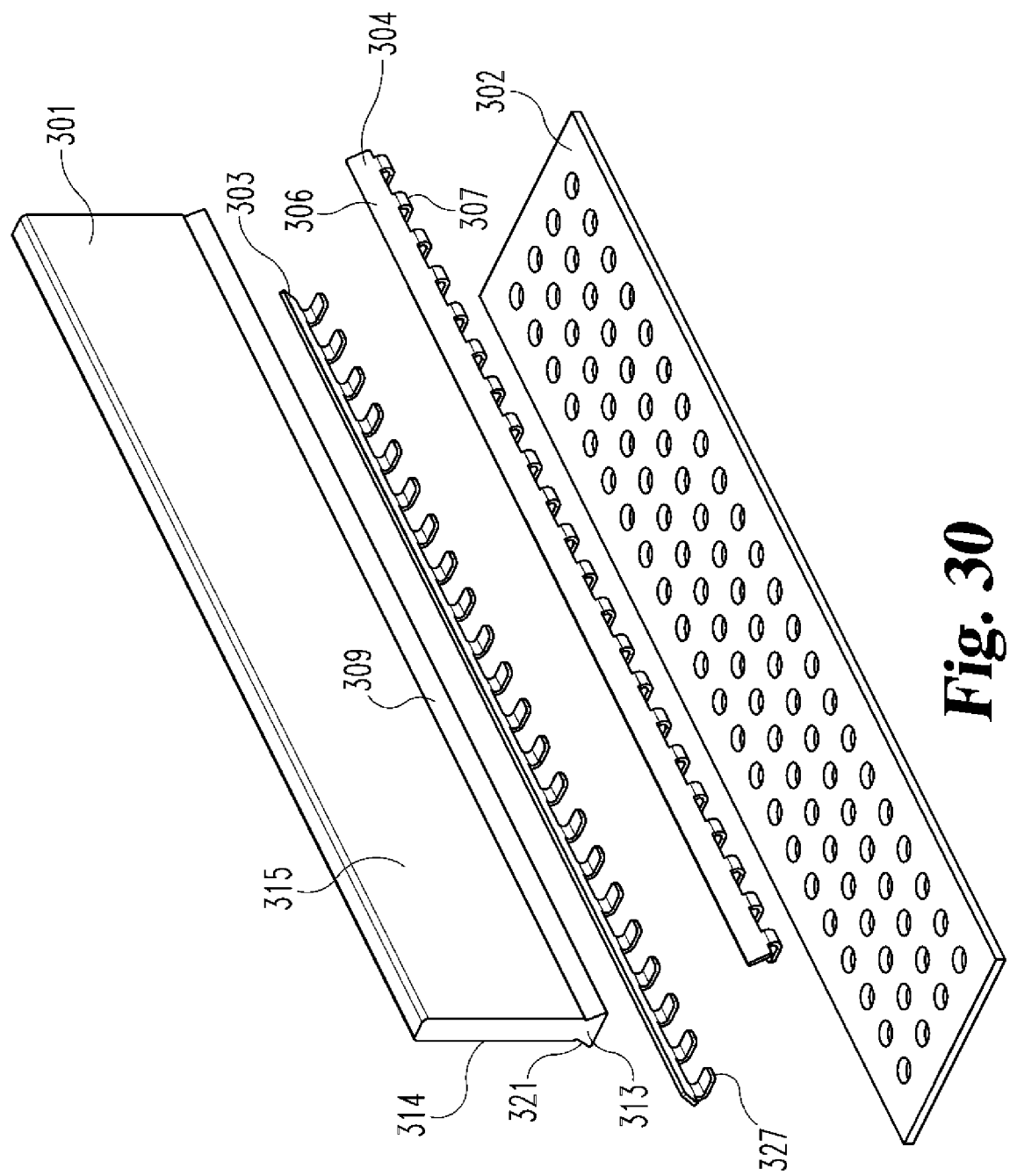
FIG. 30 is an exploded view of the device of FIG. 29.

Many variations are contemplated and included in the present invention. For example, plate 302 is shown as having four rows of holes extending the length of the plate with each of the holes arranged in a four hole pattern extending across the width of the plate. It is to be understood that a greater number or less number than the number of holes shown in FIG. 30 is contemplated and included in the present invention. Brackets 303 and 304 are shown as each having 22 legs. The number of legs attached to each bracket may be greater than or less than 22. For example, each bracket 303 and 304 may have only a pair of legs with one leg located at one end of the bracket and the second leg located at the opposite end of the bracket.

In the embodiment shown in the drawings, bar 301 has a dovetail shaped bottom end 313. Bar 301 has a pair of outwardly facing side surfaces 314 and 315. Likewise, bottom end 313 has a pair of outwardly facing side surfaces 309 and 321 that extend convergingly from the bottom surface of bottom end 313. Surfaces 314 and 315 are arranged at obtuse angles 319 and 318 relative respectively to side surfaces 321 and 309. Angles 322 and 318 must be chosen so that the inwardly facing surface 312 of main body 306 contacts and rests against the bottom side surface 309. Likewise, angles 325 and 319 must be chosen so that the inwardly facing surface 320 of bracket 303 contacts and rests against the bottom side surface 321 of bottom end 313. The inwardly facing surface 320 of bracket 303 is arranged at an acute angle 325 relative to the horizontally extending top surface 350 of legs 327. In the embodiment shown in FIG. 31, angles 318 and 319 are each 125 degrees whereas angles 322 and 325 are each 55 degrees. Angle 322 is supplementary to angle 318 and angle 325 is supplementary to angle 319 in the embodiment shown in FIG. 31 when angles 322 and 325.

Many variations are contemplated and included in the present invention. For example, the bottom end of bar 301 is shown as a dovetail shape having its enlarged end at the very bottom of the bar; however, the bottom end of the bar may take a variety of additional configurations, such as a semi-spherical shape. In any event, the inwardly facing surfaces and of brackets 303 and 304 must be configured so that they contact and extend along the bottom end of the bar to secure the bar to base wall 302.

Rigid brackets 304 and 303 each include a plurality of legs or fingers 307 and 327 (FIG. 30) that extend through the holes of base wall 302. Fingers 307 have upwardly facing surfaces contacting and extending along the bottom surface of wall 302 when rigid bracket 304 is mounted thereto. Fingers 307 and 327 have adjacent distal ends 351 and 352 (FIG. 32) separated by gap 329. Thus, fingers 307 and 327 extend toward each other when the two brackets are mounted to base wall 302 on the opposite sides of the flexible bar 301.

Figure 5:
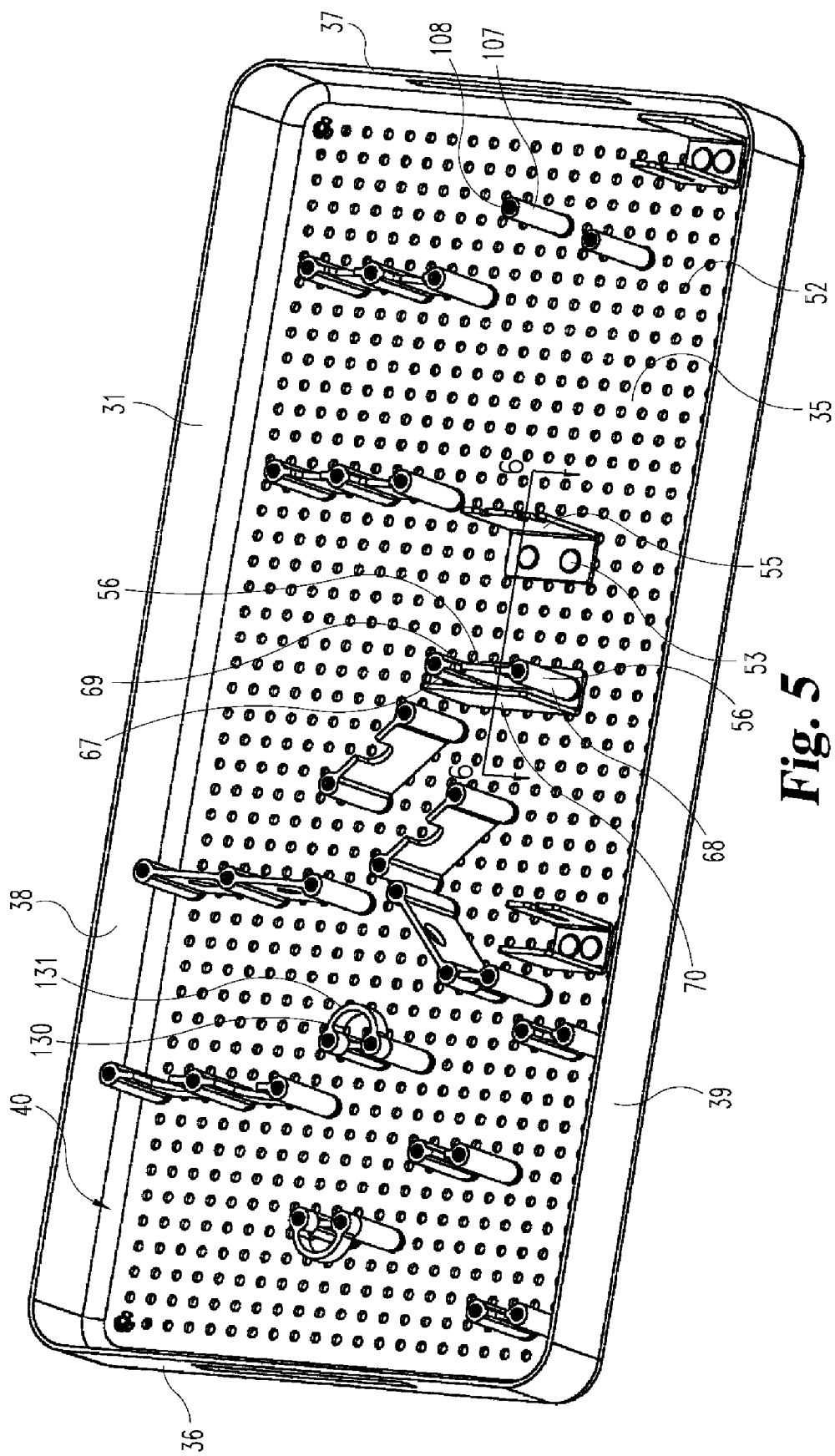
FIG. 5 is a top perspective view of the tray assembly without the cover mounted thereto illustrating examples of internal components located within the tray, as located by the fixture assembly shown in FIG. 4.
Figure 6:
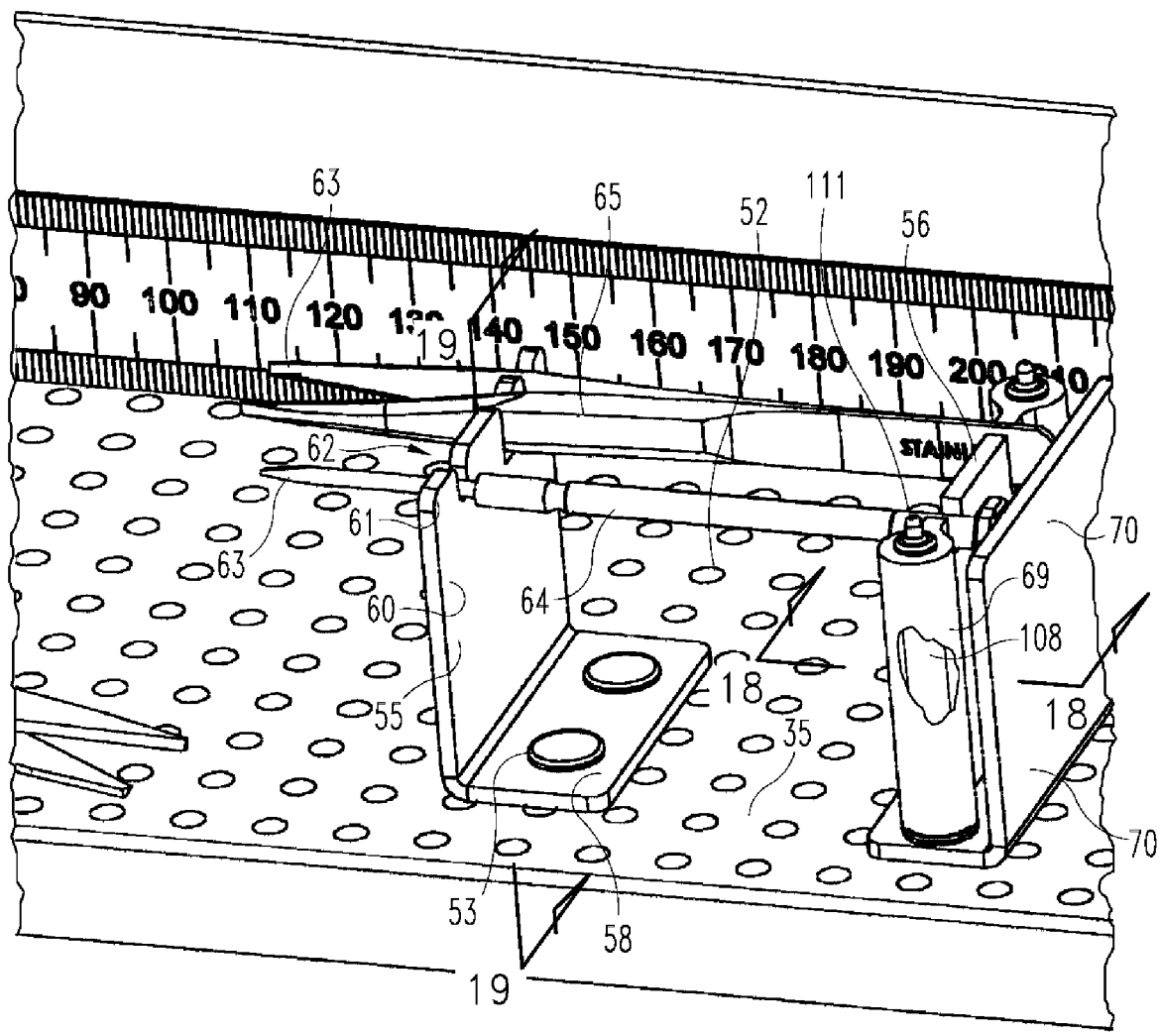
FIG. 6 is an enlarged fragmentary perspective view of two brackets mounted to the tray for holding instruments.

The flexible wall 301 and rigid brackets 303 and 304 may be mounted directly to either the floor of a container or to a separate base wall 302 that may be positioned within a container and either attached or unattached to the floor of the container. For example, base wall 302 (FIG. 31) is shown as fragmented to represent either a separate base wall 302 or floor 35 (FIG. 5). That is, the rigid brackets and wall may be directly mounted to the bottom wall 35 of container 31 (FIG.

Figure 29:
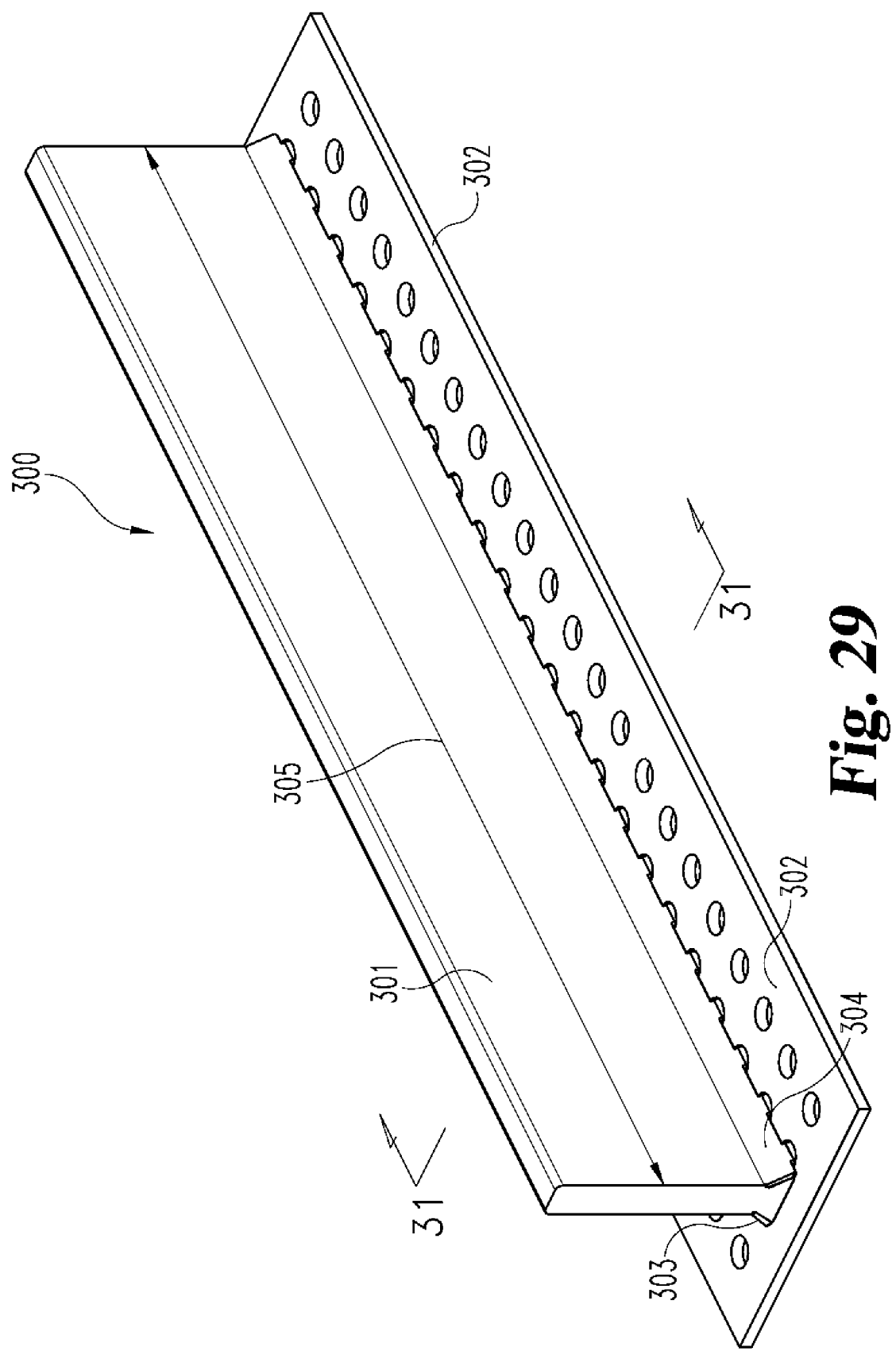
FIG. 29 is a top perspective view of an extruded flexible wall mounted to a pair of brackets, in turn, mounted to a base for partitioning a compartment or holding medical instruments and/or implants.
Figure 33:
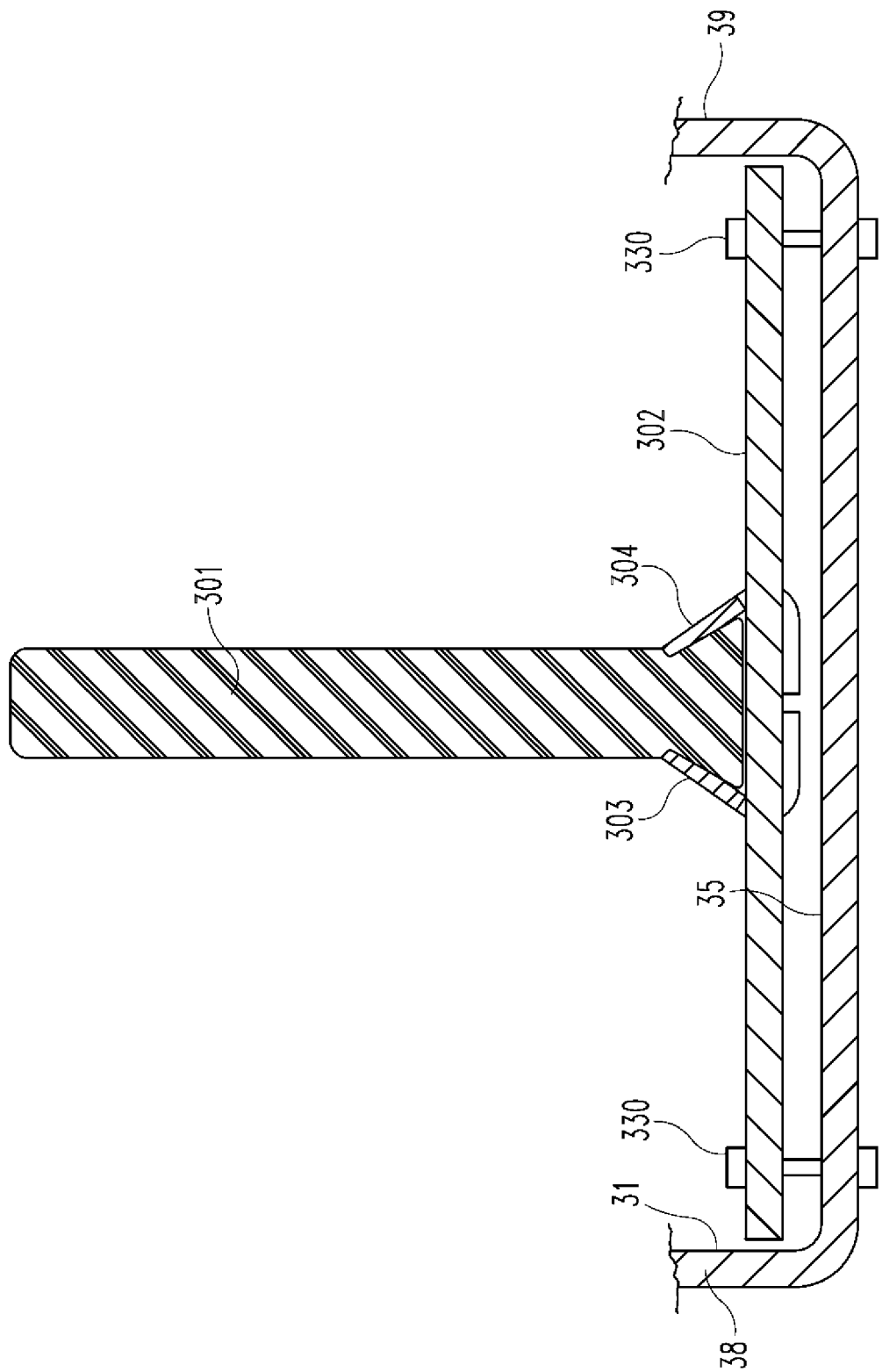
FIG. 33 is the same view as FIG. 31 only showing the device positioned within a container.
Figure 34:
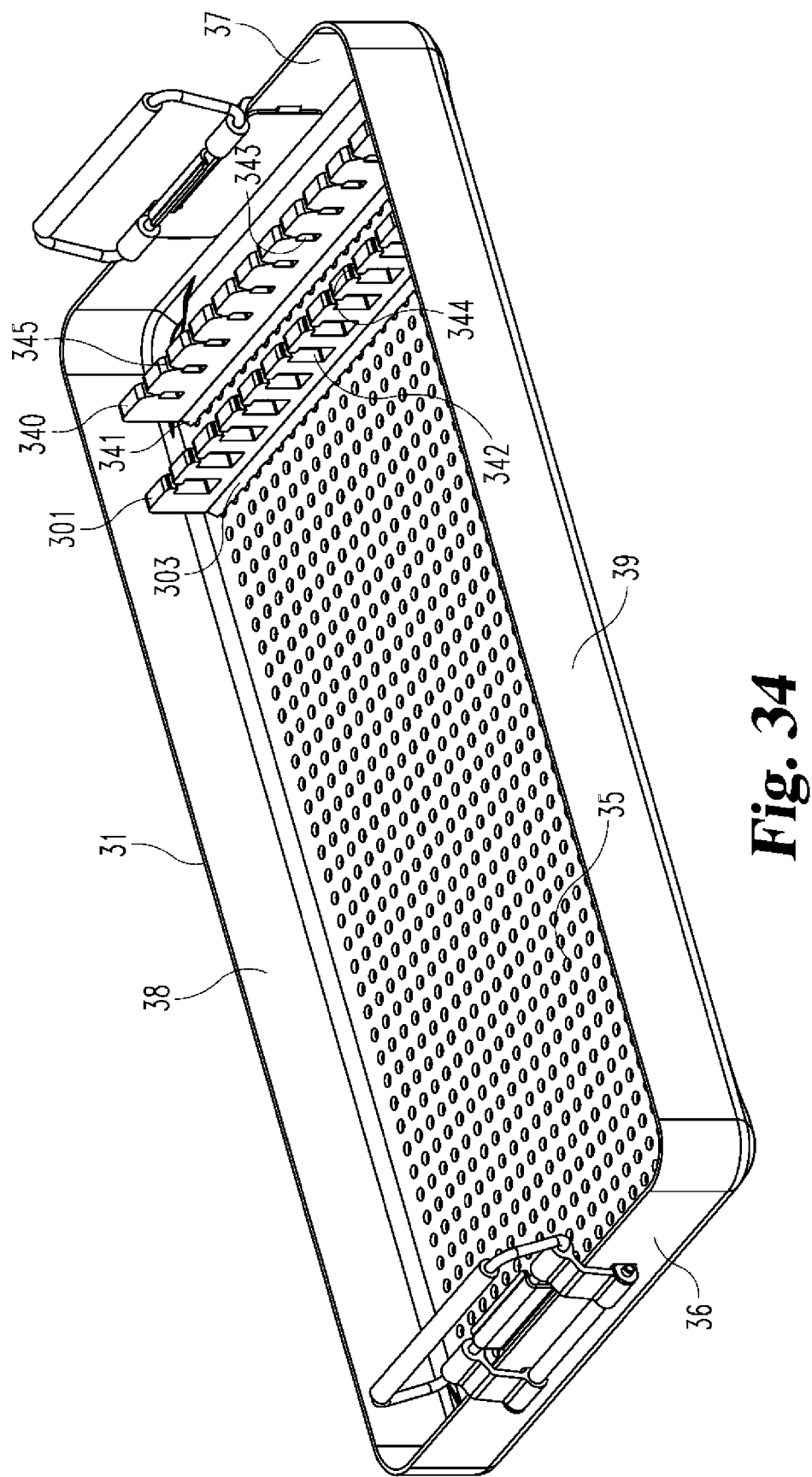
FIG. 34 is a perspective view of a container having two of the flexible bars mounted thereto.

5) without the necessity of utilizing a separate base wall 302 such as shown in FIG. 29. Alternatively, the rigid brackets 303 and 304 along with wall 301 may be mounted directly to base wall 302 which is then positioned atop wall 35 (FIG. 33) either extending across the width or the length of the container. In the embodiment shown in FIG. 33, wall 302 extends lengthwise across the width of the container and has a length approximately equal to the spacing of side walls 38 and 39. By sizing the length of base wall 302 to be approximately the distance between side walls 38 and 39, the base wall is held in place without the necessity of separate fasteners extending between wall 302 and floor 35. Alternatively, the rigid brackets and flexible wall may extend the length of container 31 between the end walls 36 and 37 (FIG. 34). In the event base wall 302 is placed atop floor 35 but does not extend the entire length of the container between end walls 36 and 37 and/or across the entire width of the container between walls 38 and 39, then it may be necessary to securely fasten base wall 302 to floor 35. In such a case, the flexible wall 301 may be used to partition the container into separate areas or compartments. Conventional fasteners 330 may be used to secure base wall 302 to floor 35 (FIG. 33).

Flexible wall 301 is particularly useful in holding medical items. For example, in FIG. 34, a pair of flexible walls 301 and 340 are shown mounted directly to the floor 35 of container 31. The two flexible walls are identical except for that the walls are cut with different recesses to conformingly fit around and hold the medical item. Thus, a pair of flexible walls 301 and 340 are each mounted by a pair of rigid brackets, in turn, mounted directly to floor 35. Thus, wall 301 includes a pair of rigid brackets 303 and 304 with the fingers of each bracket extending through the holes of floor 35 in a manner identically as previously described for wall 302. Likewise, flexible wall 340 is held by a pair of rigid brackets 341 spaced apart by a gap into which flexible wall 340 extends in a manner identical to that described for wall 301. One such rigid bracket 341 is shown in FIG. 34 it being understood that a second rigid bracket is positioned on the opposite side of wall 340. Walls 301 and 340 are parallel and are spaced apart with the medical items, not shown, extending there between. Wall 301 is shown as having a plurality of holes 342 extending through the wall allowing a medical item to extend therethrough. Likewise, flexible wall 340 includes a plurality of holes 343 extending through the flexible wall with holes 343 aligned across from holes 342. A passage extends from the top edge of each wall leading into holes 342 and 343. For example, passage 344 extends from the top edge of wall 301 into hole 342 allowing the medical instrument to be inserted through the passage and into hole 342. Likewise, passages 345 are cut into the top edge of flexible wall 340 and lead into holes 343 allowing the opposite end of the medical item to be inserted into hole 343.

Figure 31:
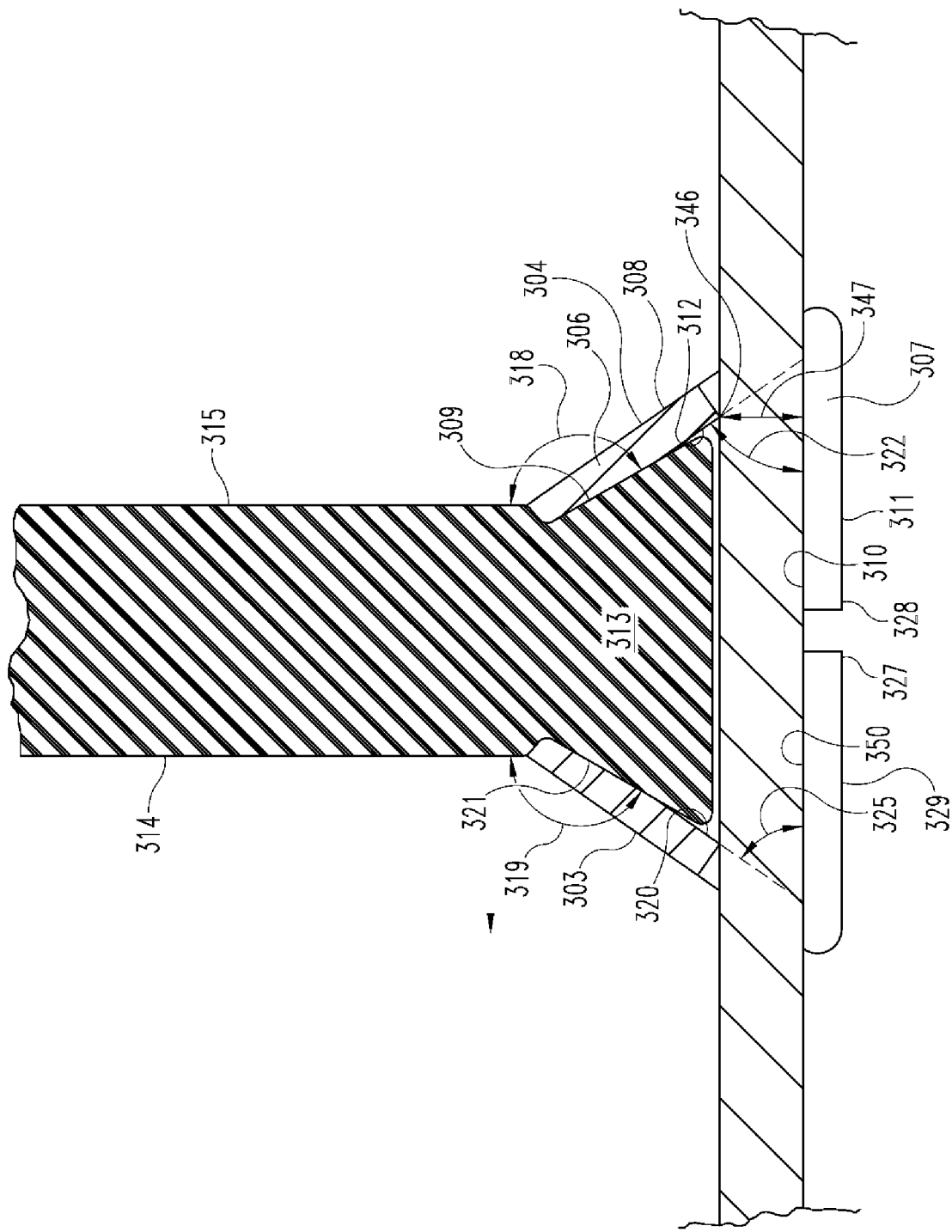
FIG. 31 is an enlarged cross-sectional view taken along the line 31-31 of FIG. 29 and viewed in the direction of the arrows.
Figure 32:
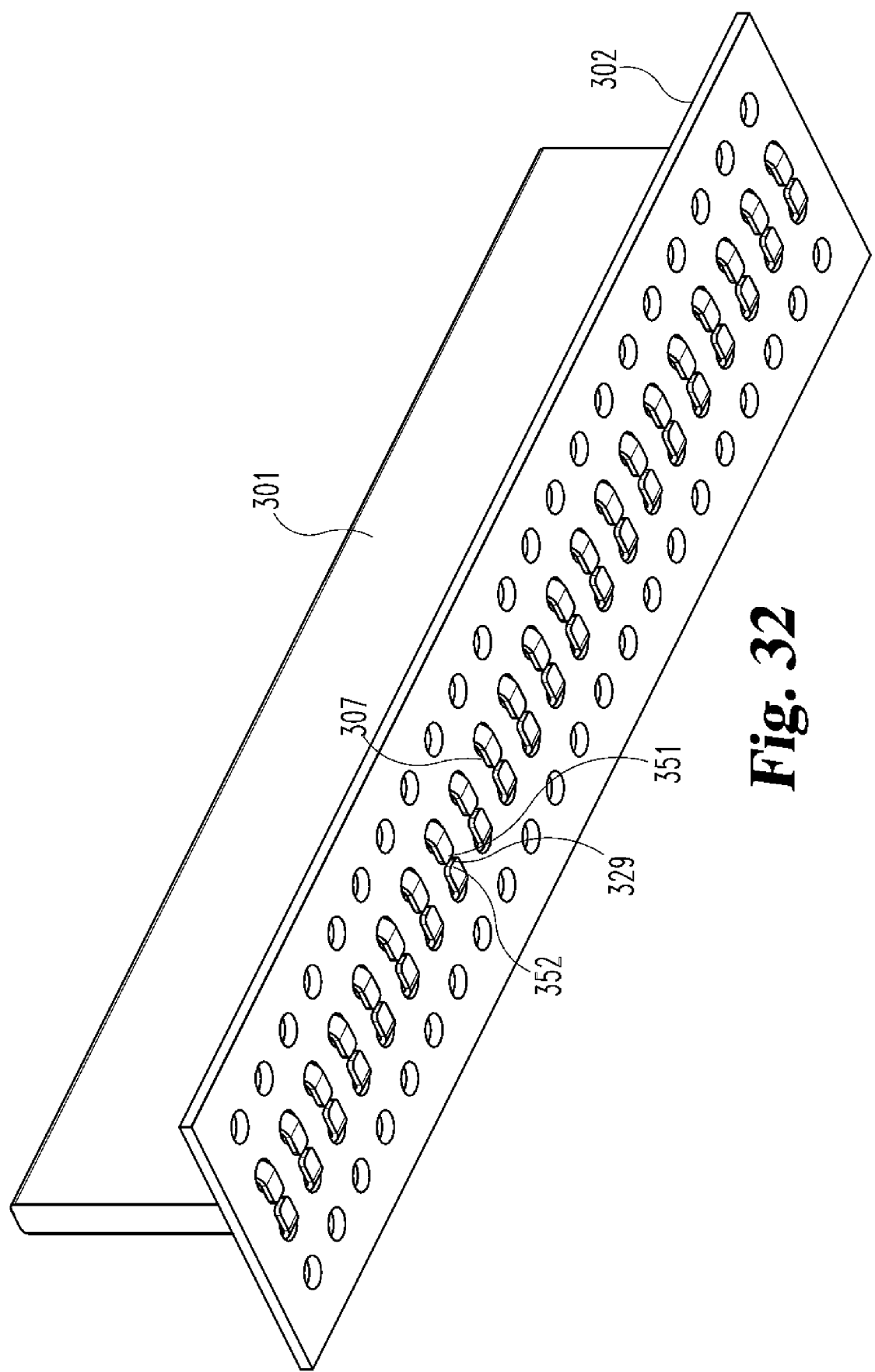
FIG. 32 is a bottom perspective view of the device of FIG. 29.

In order to mount device 300, brackets 304 and 305 are first mounted to wall 302 by inserting the feet of each bracket through the holes in wall 302. Next, the brackets are pivoted so that the upwardly facing surface of each foot is in contact with the bottom surface of wall 302 as shown in FIG. 31. Last, flexible wall 301 is slid lengthwise into the gap existing between the main bodies of the brackets. The perpendicular distance from the top of the upwardly facing surface of the feet must be equal to or only a few thousandths of an inch greater than the thickness of the wall 302. For example, for bracket 304, the distance 347 of a line perpendicular to surface 310 extending upwardly to the lowermost edge 346 of main body 306 must be equal to or slightly greater than the thickness of wall 302. Likewise, the perpendicular distance from the lowermost edge of the main body of bracket 303 must be sized the same. In the event, that the brackets are mounted directly to the container floor without floor 302, then the perpendicular distance from the lowermost edge of the bracket main bodies must be equal or only slightly greater than the thickness of the container floor. This arrangement insures that the brackets will tightly bind the flexible wall in place while allowing the flexible wall to be changed and remounted by sliding the flexible wall out of the gap between the brackets.

While the invention has been illustrated and described in detail in the drawings and foregoing description, the same is to be considered as illustrative and not restrictive in character, it being understood that only the preferred embodiments has been shown and described and that all changes and modifications that come within the spirit of the invention are desired to be protected.

What is claimed is:

1. A bracket arrangement to hold medical items on a base wall comprising:
   an elongated first bracket, said first bracket having a first main body with a plurality of first feet extending there beneath, said first main body having a first plate extending the length thereof with said first plate arranged relative to said first feet at a first angle so that when said first feet are extended through a base wall and arranged therewith position said first plate above said base wall and arranged relative to said base wall at said first angle;
   an elongated second bracket, said second bracket having a second main body with a plurality of second feet extending there beneath, said second main body having a second plate extending the length thereof and positionable to be parallel to said first plate and arranged relative to said second feet at a second angle so that when said second feet are extended through a base wall and arranged therewith position said second plate above said base wall and arranged relative to said base at said second angle; and,
   an elongated bar of flexible material extendable along the length of said first bracket and said second bracket and having a lower edge portion releasably holdable between said first bracket and said second bracket by said first plate and said second plate.

2. The bracket arrangement of claim 1 wherein:
   said first angle and said second angle are both fifty-five degrees.

3. The bracket arrangement of claim 1 wherein:
   said first main body has a downwardly facing first surface and said second main body has a downwardly facing second surface when said first feet and said second feet are mounted to said base,
   said lower edge portion of said bar has a bottom surface and a dovetail cross section with two outer surfaces converging from said bottom surface, said two outer converging surfaces fit adjacent and against said first surface of said first main body and said second surface of said second main body providing a binding fit between said bar and said first bracket and said second bracket.

4. The bracket arrangement of claim 1 wherein said bar is flexible extruded material, said first bracket and said second bracket are rigid.

5. The bracket arrangement of claim 4 wherein said extruded material is silicone rubber with said material being extruded along the length of said bar, said first bracket and said second bracket are metal or plastic.

6. The bracket arrangement of claim 1 wherein said base wall is the floor wall of a container.

7. The bracket arrangement of claim 1 wherein said base wall is positionable within a container.

8. The bracket arrangement of claim 1 wherein said first main body has a downwardly facing first surface and said second main body has a downwardly facing second surface when said first feet and said second feet are mounted to said base, said first feet and said second feet are integrally attached respectively to said first plate and said second plate, said first bracket and said second bracket when mounted to said base wall have said first feet and said second feet with surfaces facing upwardly against said base wall and said first surface and said second surface facing downwardly against said bar.

9. A container for holding medical items comprising:
a tray with a perforated floor and upwardly extending side walls forming a cavity to receive medical items;
a device positioned atop said floor within said cavity to hold a medical item, said device includes a pair of rigid brackets separated from each other said brackets spaced apart by a gap, said device further includes a flexible wall having an lengthwise extending bottom edge portion positioned within said gap and held in said cavity by said pair of brackets, said first flexible wall having a hollow portion to removably hold a medical item; said rigid brackets each including a main body and downwardly extending fingers integrally attached thereto, said fingers positioned relative to said main body at an acute angle, said fingers extend through said perforated floor locating said main body above said perforated wall and positioned relative to said perforated wall at said acute angle, said bottom edge portion of said flexible wall releasably held between and by said main body of said brackets.

10. The container of claim 9 wherein:
said flexible wall includes opposite main side surfaces facing outwardly and a bottom portion, said bottom portion includes outwardly facing lower side surfaces angularly arranged relative to said main side surfaces.

11. The container of claim 10 wherein:
each of said lower side surfaces are arranged relative to said main side surfaces at an obtuse angle, said fingers are arranged relative to said main body at an acute angle that is supplementary to said obtuse angle.

12. The container of claim 10 wherein:
said brackets include a first bracket located on one side of said flexible bar and a second bracket located on a second side of said flexible bar, said fingers of said first bracket and said second bracket extend toward each other.

13. A container for holding medical items comprising:
a tray with a perforated floor and upwardly extending side walls forming a cavity to receive medical items;
a device positioned atop said floor within said cavity to hold a medical item, said device includes a base wall positioned atop said perforated floor and a pair of rigid brackets separate from each other, said brackets spaced apart by a gap, said device further includes a flexible wall having an lengthwise extending bottom edge portion positioned within said gap and held in said cavity by said pair of brackets, said first flexible wall having a hollow portion to removably hold a medical item; each of said rigid brackets having a main body and fingers integrally attached thereto, said fingers of each of said rigid brackets engageable with said base wall to hold said brackets and said flexible wall thereto with said fingers arranged relative to said main body at an acute angle so that when said fingers are extended through said base wall position said bracket relative to said base wall at said acute angle.

14. The container of claim 13 wherein said base wall is unattached to said floor.

15. The container of claim 13 and further comprising:
a plurality of fastening devices extending through said floor and said base wall attaching said floor and said base together.

16. The container of claim 13 wherein said angle is fifty-five degrees.

17. The container of claim 16 wherein said flexible wall is silicone rubber and said brackets are metal or plastic.

18. A bracket arrangement to hold medical items on a base wall comprising:
an elongated first bracket, said first bracket having a first main body with a first foot extending there beneath, said first main body having a first plate extending the length thereof with said first plate arranged relative to said first foot at a first angle so that when said first foot is extended through a base wall and arranged therewith positions said first plate above said base wall and arranged relative to said base wall at said first angle;
an elongated second bracket, said second bracket having a second main body with a second foot extending there beneath, said second main body having a second plate extending the length thereof and positionable to be parallel to said first plate and arranged relative to said second foot at a second angle so that when said second foot is extended through a base wall and arranged therewith positions said second plate above said base wall and arranged relative to said base at said second angle; and,
an elongated bar of flexible material extendable along the length of said first bracket and said second bracket and having a lower edge portion releasably holdable between said first bracket and said second bracket by said first plate and said second plate.

* * * * *